United States Patent
Brendel et al.

(10) Patent No.: US 7,825,264 B2
(45) Date of Patent: Nov. 2, 2010

(54) SUBSTITUTED HETEROCYCLES, THEIR USE AS MEDICAMENT, AND PHARMACEUTICAL PREPARATIONS COMPRISING THEM

(75) Inventors: Joachim Brendel, Bad Vilbel (DE); Heinrich Christian Englert, Frankfurt am Main (DE); Stefan Peukert, Arlington, MA (US); Klaus Wirth, Frankfurt am Main (DE); Michael Wagner, Frankfurt am Main (DE); Jean-Marie Ruxer, Paris (FR); Fabienne Pilorge, Paris (FR)

(73) Assignee: sanofi-aventis, Paris (FR)

( * ) Notice: Subject to any disclaimer, the term of this patent is extended or adjusted under 35 U.S.C. 154(b) by 434 days.

(21) Appl. No.: 11/954,400

(22) Filed: Dec. 12, 2007

(65) Prior Publication Data
US 2008/0188520 A1     Aug. 7, 2008

Related U.S. Application Data

(63) Continuation of application No. PCT/EP2006/005579, filed on Jun. 10, 2006.

(30) Foreign Application Priority Data
Jun. 22, 2005    (DE)  ......................... 10 2005 028 845

(51) Int. Cl.
| | |
|---|---|
| C07D 215/14 | (2006.01) |
| C07D 403/06 | (2006.01) |
| C07D 295/03 | (2006.01) |
| C07D 275/02 | (2006.01) |
| C07D 211/40 | (2006.01) |
| A61K 31/55 | (2006.01) |
| A61K 31/47 | (2006.01) |
| A61K 31/4406 | (2006.01) |
| A61K 31/4015 | (2006.01) |
| A61K 31/425 | (2006.01) |
| A61K 31/45 | (2006.01) |

(52) U.S. Cl. .................... 548/530; 546/243; 546/278.4; 546/152; 548/214; 514/212.03; 514/343; 514/423; 514/372; 514/315

(58) Field of Classification Search ........................ None
See application file for complete search history.

(56) References Cited

U.S. PATENT DOCUMENTS 5,629,322 A * 5/1997 Guthikonda et al. ........ 514/313

FOREIGN PATENT DOCUMENTS

WO     WO 9614844 A1 * 5/1996

OTHER PUBLICATIONS

Moehrle et al Zeitschrift Fuer Naturforschung, B: Chemical Science 58(6) 585-594 (2003).*
Sahasrabudhe et al Journal of the American Chemical Society 125(26), 7914-7922 (2003).*
Brendel, et al., Blockers of the Kv1.5 channel for the treatment of atrial arrhythmias, Expert Opinion of therapeutic Patents; 2002; V.12, No. 11, pp. 1589-1598.
Hashimoto, et al., Stereoselective synthesis of optically active .beta.-lactams by the reaction of chiral imines derived from erythro-2-amino-1, 2-diphenytethanol with ester enolates, Heterocycles; 2000; 52(3); p. 1003.
Sahasrabudhe, et al., Asymetric Schmidt reaction of hydroxyalkyl azides with ketones, J. of the Amer. Chem. Soc., 2003, 125(26), pp. 7914-7922.

* cited by examiner

*Primary Examiner*—Kamal A Saeed
*Assistant Examiner*—Nyeemah Grazier
(74) *Attorney, Agent, or Firm*—Ronald G. Ort; Serena Farquharson-Torres; Kelly L. Bender

(57) ABSTRACT

The invention relates to compounds of formula I

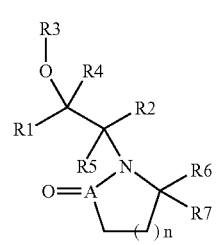

in which A, R1, R2, R3, R4, R5, R6, R7 and n have the meanings stated in the claims. The compounds are particularly suitable as antiarrhythmic active ingredients, in particular for the treatment and prophylaxis of atrial arrhythmias, for example atrial fibrillation (AF) or atrial flutter.

7 Claims, No Drawings

SUBSTITUTED HETEROCYCLES, THEIR USE AS MEDICAMENT, AND PHARMACEUTICAL PREPARATIONS COMPRISING THEM

FIELD OF THE INVENTION

The invention relates to compounds of formula I,

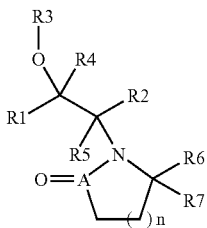

I in which A, R1, R2, R3, R4, R5, R6, R7 and n have the meanings stated below, to their preparation and their use, in particular in pharmaceuticals.

BACKGROUND OF THE INVENTION

The compounds of the invention of formula I have not previously been described. They act on the so-called Kv1.5 potassium channel and inhibit a potassium current which is designated the ultra-rapidly activating delayed rectifier in the human atrium. In addition, the compounds also act on other atrium-specific potassium channels such as the acetylcholine-dependent potassium channel KACh, and the 2P domain potassium channel TASK-1. The compounds are therefore very particularly suitable as antiarrhythmic active ingredients, in particular for the treatment and prophylaxis of atrial arrhythmias, for example atrial fibrillation (AF) or atrial flutter.

Atrial fibrillation (AF) and atrial flutter are the commonest sustained cardiac arrhythmias. The incidence increases with increasing age and frequently leads to fatal sequelae such as, for example, stroke. AF affects for example about 3 million Americans and leads to more than 80 000 strokes each year in the USA. Although class I and III antiarrhythmics currently in use can reduce the rate of recurrence of AF, their use is restricted owing to their potential proarrhythmic side effects. There is for this reason a great medical need for better medicaments for treating atrial arrhythmias to be developed.

It has been shown that so-called reentry depolarization waves underlie most supraventricular arrhythmias. Such reentries occur if the cardiac tissue has a slow conductivity and, at the same time, very short refractory periods. The increase in the myocardial refractory period by prolonging the action potential is an accepted mechanism for terminating arrhythmias and preventing their development. The length of the action potential is substantially determined by the extent of repolarizing K$^+$ currents which flow out of the cell through the various K$^+$ channels. Particularly great importance is ascribed in this connection to the so-called delayed rectifier $I_K$ which consists of 3 different components: $IK_r$, $IK_s$ and $IK_{ur}$.

Most known class III antiarrhythmics (for example dofetilide or d-sotalol) block predominantly or exclusively the rapidly activating potassium channel $IK_r$ which has been detected both in cells of the human ventricle and in the atrium. However, it has emerged that these compounds have an increased proarrhythmic risk when heart rates are low or normal, and the arrhythmias which have been observed are in particular those referred to as torsades de pointes. Besides this high risk, which is fatal in some cases, when the rate is low, the efficacy of $IK_r$ blockers has been found to decline under the conditions of tachycardia, which is just when the effect is required ("negative use-dependence").

The "particularly rapidly" activating and very slowly inactivating component of the delayed rectifier $IK_{ur}$ (=ultra-rapidly activating delayed rectifier), which corresponds to the Kv1.5 channel, is of particularly great importance for the duration of repolarization in the human atrium. Inhibition of the $IK_{ur}$ potassium outward current thus represents, by comparison with inhibition of $IK_r$ or $IK_s$, a particularly effective method for prolonging the atrial action potential and thus for terminating or preventing atrial arrhythmias. Mathematical models of the human action potential suggest that the positive effect of a blockade of the $IK_{ur}$ ought to be particularly pronounced precisely under the pathological conditions of chronic atrial fibrillation (M. Courtemanche, R. J. Ramirez, S, Nattel, Cardiovascular Research 1999, 42, 477-489: "Ionic targets for drug therapy and atrial fibrillation-induced electrical remodeling: insights from a mathematical model").

In contrast to $IK_r$ and $IK_s$, which also occur in the human ventricle, $IK_{ur}$ plays a significant role in the human atrium, but not in the ventricle. For this reason, if the $IK_{ur}$ current is inhibited, the risk of a proarrhythmic effect on the ventricle is precluded from the outset, in contrast to blockade of $IK_r$ or $IK_s$ (Z. Wang et al, Circ. Res. 73, 1993, 1061-1076: "Sustained Depolarisation-Induced Outward Current in Human Atrial Myocytes"; G.-R. Li et al, Circ. Res. 78, 1996, 689-696: "Evidence for Two Components of Delayed Rectifier K$^+$-Current in Human Ventricular Myocytes"; G. J. Amos et al, J. Physiol. 491, 1996, 31-50: "Differences between outward currents of human atrial and subepicardial ventricular myocytes").

Antiarrhythmics which act by atrium-selective blockade of the $IK_{ur}$ current or Kv1.5 channel have not, however, been available on the market to date. Although a blocking effect on the Kv1.5 channel has been described for numerous active pharmaceutical ingredients (for example quinidine, bupivacaine or propafenone), the Kv1.5 blockade in each of these cases represents only a side effect in addition to other main effects of the substances.

A number of patent applications in recent years have described various substances as Kv1.5 channel blockers. A compilation and detailed discussion of these substances has recently been published (J. Brendel, S. Peukert; Curr. Med. Chem.—Cardiovascular & Hematological Agents, 2003, 1, 273-287; "Blockers of the Kv1.5 Channel for the Treatment of Atrial Arrhythmias"). However, all Kv1.5 blockers disclosed to date and described therein have entirely different types of structures than the compounds of the invention in this application. In addition, no clinical data on the effect and tolerability in humans have been disclosed to date for any of the compounds disclosed to date. Since experience has shown that only a small proportion of active ingredients successfully overcome all the clinical hurdles from preclinical research to the medicament, there continues to be a need for novel, promising substances.

SUMMARY OF THE INVENTION

It has now been found, surprisingly, that the compounds of the invention of formula I and/or their pharmaceutically acceptable salts are potent blockers of the human Kv1.5 channel.

In addition, the compounds of formula I and/or their pharmaceutically acceptable salts also act on the acetylcholine-activated potassium channel KACh and on the TASK-1 channel, which likewise predominantly occur in the atrium (Krapivinsky G., Gordon E. A., Wickman K., Velimirovic B., Krapivinsky L., Clapham D. E.: "The G-protein-gated atrial K$^+$ channel I$_{KACh}$ is a heteromultimer of two inwardly rectifying K$^+$-channel proteins", Nature 374 (1995) 135-141; Liu, W., Saint, D. A.: "Heterogeneous expression of tandem-pore K$^+$ channel genes in adult and embryonic rat heart quantified by real-time polymerase chain reaction", Clin. Exp. Pharmacol. Physiol. 31 (2004) 174-178; Jones S. A., Morton, M. J., Hunter M., Boyett M. R.: "Expression of TASK-1, a pH-sensitive twin-pore domain K$^+$ channel, in rat myocytes", Am. J. Physiol. 283 (2002) H181-H185).

Because of this combined effect on a plurality of atrium-specific potassium channels, the compounds of formula I and/or their pharmaceutically acceptable salts can therefore be used as novel antiarrhythmics with a particularly advantageous safety profile. The compounds are suitable in particular for the treatment of supraventricular arrhythmias, for example atrial fibrillation or atrial flutter.

The compounds of formula I and/or pharmaceutically acceptable salts thereof can also be employed for the treatment and prevention of diseases where the atrium-specific potassium channels, for example the Kv1.5, the KACh and/or the TASK-1, are only partially inhibited, for example by using a lower dosage.

The compounds of formula I and/or their pharmaceutically acceptable salts can be employed to produce medicaments with a K$^+$ channel-blocking effect for the therapy and prophylaxis of K$^+$ channel-mediated diseases. The compounds of formula I and/or their pharmaceutically acceptable salts can further be used for the therapy or prophylaxis of cardiac arrhythmias which can be abolished by prolonging the action potential.

The compounds of formula I and/or their pharmaceutically acceptable salts can be employed for terminating existent atrial fibrillation or flutter to restore the sinus rhythm (cardioversion). In addition, the substances reduce the susceptibility to the development of new fibrillation events (maintenance of sinus rhythm, prophylaxis). It has further been observed that the substances are effective for preventing life-threatening ventricular arrhythmias (ventricular fibrillation) and are able to protect from sudden heart death without, however, simultaneously bringing about an unwanted prolongation of the so-called QT interval.

The compounds of formula I and/or their pharmaceutically acceptable salts can be employed for producing a medicament for the therapy or prophylaxis of reentry arrhythmias, of supraventricular arrhythmias, atrial fibrillation and/or atrial flutter.

The compounds of formula I and/or their pharmaceutically acceptable salts are further suitable for producing a medicament for the therapy or prophylaxis of heart failure, in particular of diastolic heart failure and for increasing atrial contractility.

The compounds of formula I and/or pharmaceutically acceptable salts thereof inhibit TASK potassium channels, for example the subtypes TASK-1 and TASK-3, in particular the subtype TASK-1. Because of the TASK-inhibitory properties, the compounds of formula I and/or their pharmaceutically acceptable salts are suitable for the prevention and treatment of diseases caused by activation or by an activated TASK-1, and of diseases caused secondarily by the TASK-1-related damage.

Because of the effect of the substances on the TASK channel, the compounds of formula I and/or their pharmaceutically acceptable salts are also suitable for producing a medicament for the therapy or prophylaxis of respiratory disorders, especially sleep apneas, neurodegenerative disorders and cancers, for example sleep-related respiratory disorders, central and obstructive sleep apneas, Cheyne-Stoke's breathing, snoring, impaired central respiratory drive, sudden infant death, postoperative hypoxia and apnea, muscle-related respiratory disorders, respiratory disorders following long-term ventilation, respiratory disorders associated with altitude adaptation, acute and chronic pulmonary disorders with hypoxia and hypercapnia, neurodegenerative disorders, dementia, Alzheimer's disease, Parkinson's disease, Huntington's disease, cancers, breast cancer, lung cancer, colon cancer and prostate cancer.

DETAILED DESCRIPTION OF THE INVENTION

The present invention relates to compounds of formula I

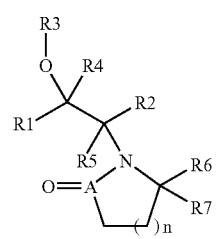

in which the meanings are:
A C, S or S=O;
n 0, 1, 2 or 3;
R1 phenyl, pyridyl, thienyl, naphthyl, quinolinyl, pyrimidinyl or pyrazinyl,
  where each of these aryl radicals is unsubstituted or substituted by 1, 2 or 3 substituents selected from the group consisting of F, Cl, Br, I, CN, alkoxy having 1, 2, 3 or 4 C atoms, OCF$_3$, methylsulfonyl, CF$_3$, alkyl having 1, 2, 3 or 4 C atoms, dimethylamino, sulfamoyl, acetyl, and methylsulfonylamino;
or
R1 cycloalkyl having 3, 4, 5, 6 or 7 C atoms;
R2 phenyl, pyridyl, thienyl, naphthyl, quinolinyl, pyrimidinyl or pyrazinyl, where each of these aryl radicals is unsubstituted or substituted by 1, 2 or 3 substituents selected from the group consisting of F, Cl, Br, I, CN, COOMe, CONH$_2$, alkoxy having 1, 2, 3 or 4 C atoms, OCF$_3$, OH, methylsulfonyl, CF$_3$, alkyl having 1, 2, 3 or 4 C atoms, dimethylamino, sulfamoyl, acetyl, and methylsulfonylamino;
R3 C$_p$H$_{2p}$—R8;
  p 0, 1, 2, 3, 4 or 5;
  R8 CH$_3$, CH$_2$F, CHF$_2$, CF$_3$, cycloalkyl having 3, 4, 5, 6 or 7 C atoms, C≡CH, C≡C—CH$_3$, alkoxy having 1, 2, 3 or 4 C atoms, phenyl or pyridyl,
    where phenyl and pyridyl are unsubstituted or substituted by 1, 2 or 3 substituents selected from the group consisting of F, Cl, Br, I, CF$_3$, OCF$_3$, CN, COOMe, CONH$_2$, COMe, OH, alkyl having 1, 2, 3 or 4 C atoms, alkoxy having 1, 2, 3 or 4 C atoms, dimethylamino, sulfamoyl, methylsulfonyl and methylsulfonylamino;

R4 hydrogen or alkyl having 1, 2 or 3 C atoms;
R5 hydrogen or alkyl having 1, 2 or 3 C atoms;
R6 and R7
  independently of one another hydrogen, F or alkyl having 1, 2, or 3 C atoms; and the pharmaceutically acceptable salts and trifluoroacetates thereof.

Compounds of formula I preferred in one embodiment are those in which the meanings are:
A C, S or S=O;
n 0, 1, 2 or 3;
R1 phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl,
  where each of these aryl radicals is unsubstituted or substituted by 1, 2 or 3 substituents selected from the group consisting of F, Cl, Br, I, CN, alkoxy having 1, 2, 3 or 4 C atoms, $OCF_3$, methylsulfonyl, $CF_3$, alkyl having 1, 2, 3 or 4 C atoms, dimethylamino, sulfamoyl, acetyl, and methylsulfonylamino;
or
R1 cyclohexyl;
R2 phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl,
  where each of these aryl radicals is unsubstituted or substituted by 1, 2 or 3 substituents selected from the group consisting of F, Cl, Br, I, CN, COOMe, $CONH_2$, alkoxy having 1, 2, 3 or 4 C atoms, $OCF_3$, OH, methylsulfonyl, $CF_3$, alkyl having 1, 2, 3 or 4 C atoms, dimethylamino, sulfamoyl, acetyl, and methylsulfonylamino;
R3 $C_pH_{2p}$—R8;
  p 0, 1, 2, 3, 4 or 5;
  R8 $CH_3$, $CH_2F$, $CHF_2$, $CF_3$, cycloalkyl having 3, 4, 5, 6 or 7 C atoms, C≡CH, C≡C—$CH_3$, alkoxy having 1, 2, 3 or 4 C atoms, phenyl or 2-pyridyl,
    where phenyl and 2-pyridyl are unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 C atoms, alkoxy having 1, 2, 3 or 4 C atoms, dimethylamino, sulfamoyl, methylsulfonyl and methylsulfonylamino;
R4 hydrogen or alkyl having 1, 2 or 3 C atoms;
R5 hydrogen or alkyl having 1, 2 or 3 C atoms;
R6 and R7
  independently of one another hydrogen, F or alkyl having 1, 2, or 3 C atoms; and the pharmaceutically acceptable salts and trifluoroacetates thereof.

Particularly preferred compounds of formula I are those in which
A is C or S=O;
n is 0, 1, 2 or 3;
R1 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl or 8-quinolinyl,
  where each of these aryl radicals is unsubstituted or substituted by 1 or 2 substituents selected from the group consisting of F, Cl, Br, I, CN, alkoxy having 1, 2, 3 or 4 C atoms, $OCF_3$, methylsulfonyl, $CF_3$ and alkyl having 1, 2, 3 or 4 C atoms;
or
R1 is cyclohexyl;
R2 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl or 8-quinolinyl,
  where each of these aryl radicals is unsubstituted or substituted by 1 or 2 substituents selected from the group consisting of Cl, Br, I, CN, $CF_3$, alkyl having 1, 2, 3 or 4 C atoms;
R3 is $C_pH_{2p}$—R8;
  p is 0, 1, 2, 3 or 4;
  R8 is $CH_3$, $CH_2F$, $CHF_2$, $CF_3$, cycloalkyl having 3, 4, 5 or 6 C atoms, C≡CH, C≡C—$CH_3$, alkoxy having 1, 2, 3 or 4 C atoms, phenyl or 2-pyridyl,
    where phenyl and 2-pyridyl are unsubstituted or substituted by 1 or 2 substituents selected from the group consisting of F, Cl, Br, I, $CF_3$, $OCF_3$, CN, COOMe, $CONH_2$, COMe, OH, alkyl having 1, 2, 3 or 4 C atoms and alkoxy having 1, 2, 3 or 4 C atoms;
R4 is hydrogen or alkyl having 1, 2 or 3 C atoms;
R5 is hydrogen or alkyl having 1, 2 or 3 C atoms;
R6 and R7
  are independently of one another hydrogen, F or alkyl having 1, 2, or 3 C atoms;

and the pharmaceutically acceptable salts and trifluoroacetates thereof.

One embodiment describes compounds of formula I in which A is defined as C or SO, for example as C.

A further embodiment describes compounds of formula I in which n is 1 or 2.

A further embodiment describes compounds of formula I in which R1 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl, 4-pyridazinyl or cyclohexyl, preferably phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl or cyclohexyl, for example phenyl, 3-pyridyl, 4-pyridyl, 1-naphthyl, 8-quinolinyl or cyclohexyl, where each of the aryl radicals, for example phenyl, is unsubstituted or substituted by 1, 2 or 3 substituents selected from the group consisting of F, Cl, Br, I, CN, alkoxy having 1, 2, 3 or 4 C atoms, $OCF_3$, methylsulfonyl, $CF_3$, alkyl having 1, 2, 3 or 4 C atoms, dimethylamino, sulfamoyl, acetyl, and methylsulfonylamino, preferably F, Cl, Br, I, CN, alkoxy having 1, 2, 3 or 4 C atoms, $OCF_3$, methylsulfonyl, $CF_3$ and alkyl having 1, 2, 3 or 4 C atoms; R1 is defined for example as phenyl, 3-pyridyl, 4-pyridyl, 1-naphthyl, 8-quinolinyl or cyclohexyl, where phenyl is unsubstituted or substituted by 1 or 2 substituents selected from the group of F, Cl, methoxy, $OCF_3$, methylsulfonyl or $CF_3$.

A further embodiment describes compounds of formula I in which R2 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl, preferably phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl or 8-quinolinyl, for example phenyl, 2-pyridyl, 3-pyridyl, 2-thienyl or 8-quinolinyl, where each of these aryl radicals is unsubstituted or substituted by 1, 2 or 3 substituents selected from the group consisting of F, Cl, Br, I, CN, COOMe, CONH$_2$, alkoxy having 1, 2, 3 or 4 C atoms, OCF$_3$, OH, methylsulfonyl, CF$_3$, alkyl having 1, 2, 3 or 4 C atoms, dimethylamino, sulfamoyl, acetyl, and methylsulfonylamino, preferably F, Cl, Br, I, CN, CF$_3$, alkyl having 1, 2, 3 or 4 C atoms; R1 is for example defined as phenyl, 2-pyridyl, 3-pyridyl, 2-thienyl or 8-quinolinyl, where phenyl and 2-thienyl are unsubstituted or substituted by 1 or 2, preferably 1, substituents selected from the group of F and methyl.

One embodiment describes compounds of formula I in which R3 is C$_p$H$_{2p}$—R8, where p is 0, 1, 2, 3 or 4, for example 0, 1, 2 or 3, and R8 is CH$_3$, CH$_2$F, CHF$_2$, CF$_3$, cycloalkyl having 3, 4, 5 or 6 C atoms, C≡CH, C≡C—CH$_3$, alkoxy having 1, 2, 3 or 4 C atoms, phenyl or 2-pyridyl, for example CH$_3$, CH$_2$F, CF$_3$, cyclopropyl, C≡CH, C≡C—CH$_3$, phenyl or 2-pyridyl, where phenyl and 2-pyridyl, for example phenyl, are unsubstituted or substituted by 1 or 2 substituents selected from the group consisting of F, Cl, Br, I, CF$_3$, OCF$_3$, CN, COOMe, CONH$_2$, COMe, OH, alkyl having 1, 2, 3 or 4 C atoms, alkoxy having 1, 2, 3 or 4 C atoms, dimethylamino, sulfamoyl, methylsulfonyl and methylsulfonylamino, preferably F, Cl, Br, I, CF$_3$, OCF$_3$, CN, COOMe, CONH$_2$, COMe, OH, alkyl having 1, 2, 3 or 4 C atoms and alkoxy having 1, 2, 3 or 4 C atoms, for example, Cl, CN, COMe and methoxy; R3 is for example defined as CH$_3$, CH$_2$F, CF$_3$, cyclopropyl, C≡CH, C≡C—CH$_3$, phenyl or 2-pyridyl, where phenyl is unsubstituted or substituted by 1 or 2, preferably 1, substituents selected from the group of Cl, CN, COMe and methoxy.

A further embodiment describes compounds of formula I in which R4 is hydrogen or methyl, for example hydrogen.

A further embodiment describes compounds of formula I in which R5 is hydrogen or methyl, for example hydrogen.

A further embodiment describes compounds of formula I in which one of the substituents R4 and R5 is methyl and the other is hydrogen, or R4 and R5 are hydrogen.

A further embodiment describes compounds of formula I in which R6 and R7 are independently of one another hydrogen or methyl, for example hydrogen. A further embodiment describes compounds of formula I in which one of the substituents R6 and R7 is methyl and the other is hydrogen, or R6 and R7 are hydrogen.

The compounds of formula I may exist in stereoisomeric forms. The centers of asymmetry which are present may independently of one another have the S configuration or the R configuration. The invention includes all possible stereoisomers, for example enantiomers or diastereomers, and mixtures of two or more stereoisomeric forms, for example enantiomers and/or diastereomers, in any ratios. The invention thus includes for example enantiomers in enantiopure form, both as levorotatory and as dextrorotatory antipodes, and in the form of mixtures of the two enantiomers in various ratios or in the form of racemates. Individual stereoisomers can be prepared as desired by fractionating a mixture by conventional methods or for example by stereoselective synthesis.

If mobile hydrogen atoms are present, the present invention also includes all tautomeric forms of compounds of formula I.

The present invention further includes derivatives of compounds of formula I, for example solvates, such as hydrates and alcohol adducts, esters, prodrugs and other physiologically acceptable derivatives of the compounds of formula I, and active metabolites of the compounds of formula I. The invention likewise includes all crystal modifications of the compounds of formula I.

Alkyl radicals and alkylene radicals may be straight-chain or branched. This also applies to the alkylene radicals of formula C$_p$H$_{2p}$. Alkyl radicals and alkylene radicals may also be straight-chain or branched if they are substituted or are present in other radicals, for example in an alkoxy radical or in a fluorinated alkyl radical. Examples of alkyl radicals are methyl, ethyl, n-propyl, isopropyl, n-butyl, isobutyl, sec-butyl and tert-butyl. The divalent radicals derived from these radicals, for example methylene, 1,1-ethylene, 1,2-ethylene, 1,1-propylene, 1,2-propylene, 2,2-propylene, 1,3-propylene, 1,1-butylene, 1,4-butylene, etc. are examples of alkylene radicals. One or more, for example 1, 2, 3, 4, 5, 6, 7, 8, or 9 hydrogen atoms in alkyl and alkylene radicals may be replaced by fluorine atoms. Substituted alkyl radicals may be substituted in any positions.

Cycloalkyl radicals may likewise be branched. Examples of cycloalkyl radicals having 3 to 7 C atoms are cyclopropyl, cyclobutyl, 1-methylcyclopropyl, 2-methylcyclopropyl, cyclopentyl, 2-methylcyclobutyl, 3-methylcyclobutyl, cyclopentyl, cyclohexyl, 2-methylcyclohexyl, 3-methylcyclohexyl, 4-methylcyclohexyl, cycloheptyl etc. One or more, for example 1, 2, 3, 4, 5, 6, 7, 8, 9, 10, 11, 12, 13 or 14 hydrogen atoms in cycloalkyl radicals may be replaced by fluorine atoms. Substituted cycloalkyl radicals may be substituted in any positions. Cycloalkyl radicals may also be in branched form as alkylcycloalkyl or cycloalkylalkyl, for example methylcyclohexyl or cyclohexylmethyl. Phenyl radicals may be unsubstituted or substituted one or more times, for example once, twice or three times, by identical or different radicals. If a phenyl radical is substituted, it preferably has one or two identical or different substituents. Monosubstituted phenyl radicals may be substituted in position 2, 3 or 4, disubstituted in 2,3-, 2,4-, 2,5-, 2,6-, 3,4- or 3,5-position trisubstituted in 2,3,4-, 2,3,5-, 2,3,6-, 2,4,5-, 2,4,6- or 3,4,5 position. A corresponding statement applies analogously also to the N-containing heteroaromatic systems such as pyridyl, quinolinyl, pyrimidinyl or pyrazinyl, the naphthyl radical and the thienyl radical, for example for 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl.

If a radical is di- or trisubstituted, the substituents may be identical or different.

If the compounds of formula I comprise one or more basic groups or one or more basic heterocycles, the invention also includes the corresponding physiologically, pharmaceutically or toxicologically acceptable salts, especially the pharmaceutically acceptable salts, but also the trifluoroacetates. Thus, the compounds of formula I which have one or more basic, i.e. protonatable, groups or comprise one or more basic heterocyclic rings, can also be used in the form of their physiologically tolerated acid addition salts with inorganic or organic acids, for example as hydrochlorides, phosphates, sulfates, methanesulfonates, acetates, lactates, maleates, fumarates, malates, gluconates etc. Salts can be obtained from compounds of formula I by conventional processes, for example by combining with an acid in a solvent or dispersant or else by anion exchange from other salts. The compounds of formula I may also be deprotonated on an acidic group and be used for example as alkali metal salts, preferably sodium or potassium salts, or as ammonium salts, for example as salts with ammonia or organic amines or amino acids.

The invention further relates to processes for preparing the compounds of formula I. The compounds of formula I can be prepared by various chemical processes, for example starting from 2-amino-1,2-diarylethanols of formula II as outlined in scheme 1 or 2, where A, R1, R2, R3, R4, R5, R6, R7 and n have the meaning indicated above, and Y is a leaving group such as, for example, Cl, Br, I, tosylate, mesylate in the case of an aliphatic radical R3 or additionally also F in the case of an aromatic radical R3.

Scheme 1

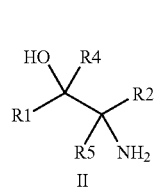 + 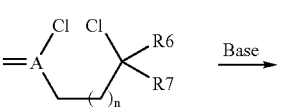 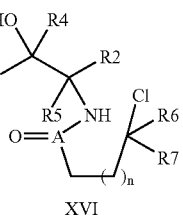

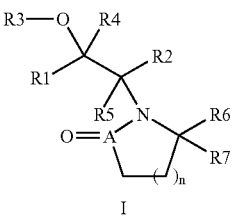

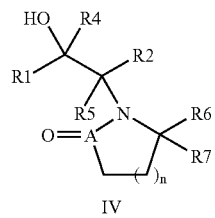 + 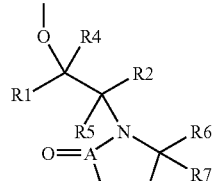

For the conversion shown in scheme 1, initially a compound of formula II is reacted with a compound of formula III in the presence of a base, for example sodium hydroxide. The resulting compound of formula IV is subsequently reacted with a compound of formula V in the presence of a base, for example sodium hydride or potassium hydroxide, to give the desired compound of formula I.

Scheme 2

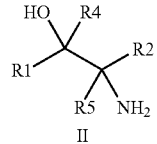 + 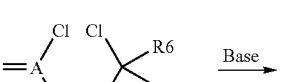

For the conversion shown scheme 2, initially a compound of formula II is reacted with a compound of formula III in the presence of a base, for example sodium bicarbonate. The resulting compound of formula XVI is subsequently mixed with a base, for example sodium hydroxide, and this mixture is reacted with a compound of formula V to give the desired compound of formula I.

A further method for preparing compounds of formula I is in scheme 3 below, where A, R1, R2, R3, R4, R5, R6, R7 and n have the meaning indicated above, and Y is a leaving group such as, for example, Cl, Br, I, tosylate, mesylate in the case of an aliphatic radical R3 or additionally also F in the case of an aromatic radical R3.

Scheme 3

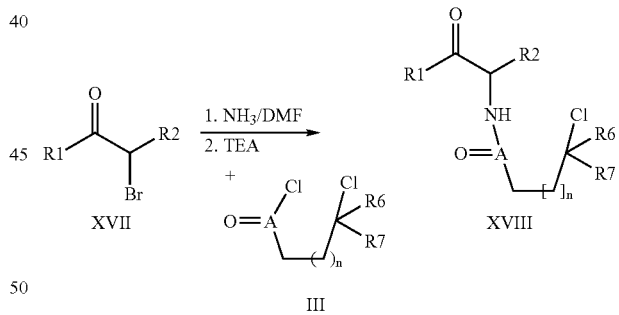

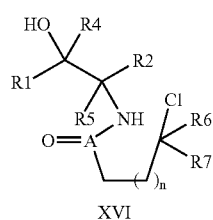 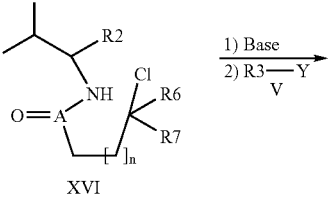

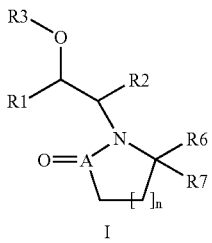

To prepare compounds of formula I as shown in scheme 3, initially a bromo ketone of formula XVII is mixed with NHE$_3$ and subsequently reacted with a compound of formula III. The resulting compound of formula XVIII is reduced with NaBH$_4$ to give the compound of formula XVI. The resulting compound of formula XVI is subsequently mixed with a base, for example sodium hydroxide, and this mixture is reacted with a compound of formula V to give the desired compound of formula I.

The 2-amino-1,2-diarylethanols of formula II employed can either be purchased, are known from the literature or can be prepared in analogy to synthetic methods disclosed in the literature for preparing 1,2-amino alcohols. Exemplary methods for synthesizing compounds of formula II and their subsequent conversion into the compounds of the invention of formula I are detailed hereinafter in the experimental section. The compounds of formula III, V and XVII can likewise either be purchased, are disclosed in the literature or can be prepared by synthetic methods known to the skilled worker.

The working up and, if desired, the purification of the products and/or intermediates takes place by conventional methods such as extraction, chromatography or crystallization and conventional dryings.

The use of the compounds of formula I and their pharmaceutically acceptable salts as medicament is claimed.

The compounds of the invention of formula I and their pharmaceutically acceptable salts can thus be used on animals, preferably on mammals, and in particular on humans, as pharmaceuticals on their own, in mixtures with one another or in the form of pharmaceutical preparations.

The present invention also relates to the compounds of formula I and their pharmaceutically acceptable salts for use in the therapy and prophylaxis of the abovementioned diseases and to their use for producing medicaments for the abovementioned diseases and medicaments with a K$^+$ channel-blocking action.

Also claimed is a pharmaceutical preparation comprising an effective amount of a compound of formula I and/or of its pharmaceutically acceptable salts, together with pharmaceutically acceptable carriers and additives, alone or in combination with other pharmacological active ingredients or pharmaceuticals. The pharmaceutical preparations normally comprise from 0.1 to 90 percent by weight of the compounds of formula I and/or their pharmaceutically acceptable salts. The pharmaceutical preparations can be produced in a manner known per se. For this purpose, the compounds of formula I and/or their pharmaceutically acceptable salts are converted together with one or more solid or liquid pharmaceutical vehicles and/or excipients and, if desired, in combination with other pharmaceutical active ingredients into a suitable dosage form, which can then be used as pharmaceutical in human medicine or veterinary medicine.

Pharmaceuticals which comprise a compound of formula I and/or its pharmaceutically acceptable salts can moreover be administered for example orally, parenterally, intravenously, rectally, percutaneously, topically or by inhalation, and the preferred administration depends on the individual case, for example on the particular manifestation of the disorder. The compounds of formula I can moreover be used alone or together with pharmaceutical excipients, in particular both in veterinary and in human medicine. The pharmaceuticals comprise active ingredients of formula I and/or their pharmaceutically acceptable salts generally in an amount of from 0.01 mg to 1 g per dose unit.

The skilled worker is familiar on the basis of his expert knowledge with which excipients are suitable for the desired pharmaceutical formulation. Besides solvents, gel formers, suppository bases, tablet excipients and other active substance carriers it is possible to use for example antioxidants, dispersants, emulsifiers, antifoams, masking flavors, preservatives, solubilizers, agents for achieving a depot effect, buffer substances or colorants.

For a form for oral use, the active compounds are mixed with the additives suitable for this purpose, such as carriers, stabilizers or inert diluents, and converted by conventional methods into suitable presentations such as tablets, coated tablets, two-piece capsules, aqueous, alcoholic or oily solutions. Examples of inert carriers which can be used are gum arabic, magnesia, magnesium carbonate, potassium phosphate, lactose, glucose or starch, especially corn starch. Preparation can take place both as dry and as wet granules. Suitable as oily carriers or as solvents are, for example, vegetable or animal oils such as sunflower oil or fish liver oil. Suitable solvents for aqueous or alcoholic solutions are, for example, water, ethanol or sugar solutions or mixtures thereof. Examples of further excipients, also for other administration forms, are polyethylene glycols and polypropylene glycols.

For subcutaneous, intramuscular or intravenous administration, the active compounds are converted if desired with the substances usual for this purpose, such as solubilizers, emulsifiers or further excipients, into a solution, suspension or emulsion. The compounds of formula I and/or their pharmaceutically acceptable salts may also be lyophilized and the resulting lyophilizates be used, for example, for producing products for injection or infusion. Examples of suitable solvents are: water, physiological saline or alcohols, for example ethanol, propanol, glycerol, as well as sugar solutions such as glucose or mannitol solutions, or else mixtures of the various solvents mentioned.

Suitable as pharmaceutical formulations for administration in the form of aerosols or sprays are, for example, solutions, suspensions or emulsions of the active ingredient of formula I or their pharmaceutically acceptable salts in a pharmaceutically acceptable solvent, such as in particular ethanol or water, or a mixture of such solvents. The formulation may if required also comprise other pharmaceutical excipients such as surfactants, emulsifiers and stabilizers, and a propellant gas. Such a preparation comprises the active ingredient normally in a concentration of about 0.1 to 10, in particular of about 0.3 to 3 percent by weight.

The dosage of the active ingredient to be administered or of the pharmaceutically acceptable salts thereof depends on the individual case and should be adapted to the circumstances of the individual case as usual for an optimal effect. Thus, it naturally depends on the frequency of administration and on the potency and duration of action of the particular compounds employed for therapy or prophylaxis, but also on the type and severity of the disease to be treated, and on the gender, age, weight and individual response of the human or animal to be treated, and on whether therapy is acute or prophylactic.

The daily dose of a compound of formula I and/or its pharmaceutically acceptable salts for a patient weighing about 75 kg is normally at least 0.001 mg/kg to 100 mg/kg of body weight, preferably 0.01 mg/kg to 20 mg/kg. Even higher dosages may also be necessary for acute episodes of the disease, for example in an intensive care unit. Up to 800 mg per day may be necessary, especially on i.v. use, for instance for an infarct patient in an intensive care unit. The dose may be in the form of a single dose or be divided into a plurality, for example two, three or four, single doses. Parenteral administration by injection or infusion, for example a continuous intravenous infusion, may also be advantageous, especially in the treatment of acute cases of cardiac arrhythmias, for example in an intensive care unit.

The compounds of formula I and/or their pharmaceutically acceptable salts can also be combined with other pharmaceutical active ingredients to achieve an advantageous therapeutic effect. Thus, advantageous combinations with substances acting on the cardiovascular system are possible in the treatment of cardiovascular disorders. Suitable examples of such combination partners advantageous for cardiovascular disorders are other antiarrhythmics, i.e. class I, class II or class III antiarrhythmics, such as, for example, $IK_r$ channel blockers, for example dofetilide, or additionally substances which reduce blood pressure, such as ACE inhibitors (for example enalapril, captopril, ramipril), angiotensin antagonists, $K^+$ channel activators, and alpha- and beta-receptor blockers, but also sympathomimetic and adrenergic compounds, and $Na^+/H^+$ exchange inhibitors, calcium channel antagonists, phosphodiesterase inhibitors and other substances with a positive inotropic effect, such as, for example, digitalis glycosides, or diuretics. In particular, combinations with beta blockers or $IK_r$ channel blockers are of particular interest.

List of Abbreviations:
TMSCl Trimethylsilyl chloride
TFA Trifluoroacetic acid
Et Ethyl
DMF N,N-Dimethylformamide
TEA Triethylamine
DMSO Dimethyl sulfoxide
THF Tetrahydrofuran The compounds of formula I can be prepared by various processes. The preparation methods used to prepare the examples are described below, where R1, R2, R3, R4, R5, R6 and X have the same meaning as in compounds of formula I.

The compounds of formula I can be prepared by various processes. The preparation methods used to prepare the examples are described below, where A, R1, R2, R3, R4, R5, R6, R7 and n have the same meaning as in compounds of formula I.

Preparation of 2-amino-1,2-diarylethanols

The following 2-amino-1,2-diarylethanols were obtained from commercial sources:
(1S,2R)-2-amino-1,2-diphenylethanol,
(1R,2S)-2-amino-1,2-diphenylethanol,
(1R,2R)-2-amino-1,2-diphenylethanol and
(1S,2S)-2-amino-1,2-diphenylethanol.

All other 2-amino-1,2-diarylethanols were prepared by one of the following methods A1, A2 or A3.

General Methods for Synthesizing 2-amino-1,2-diarylethanols

Method A1:

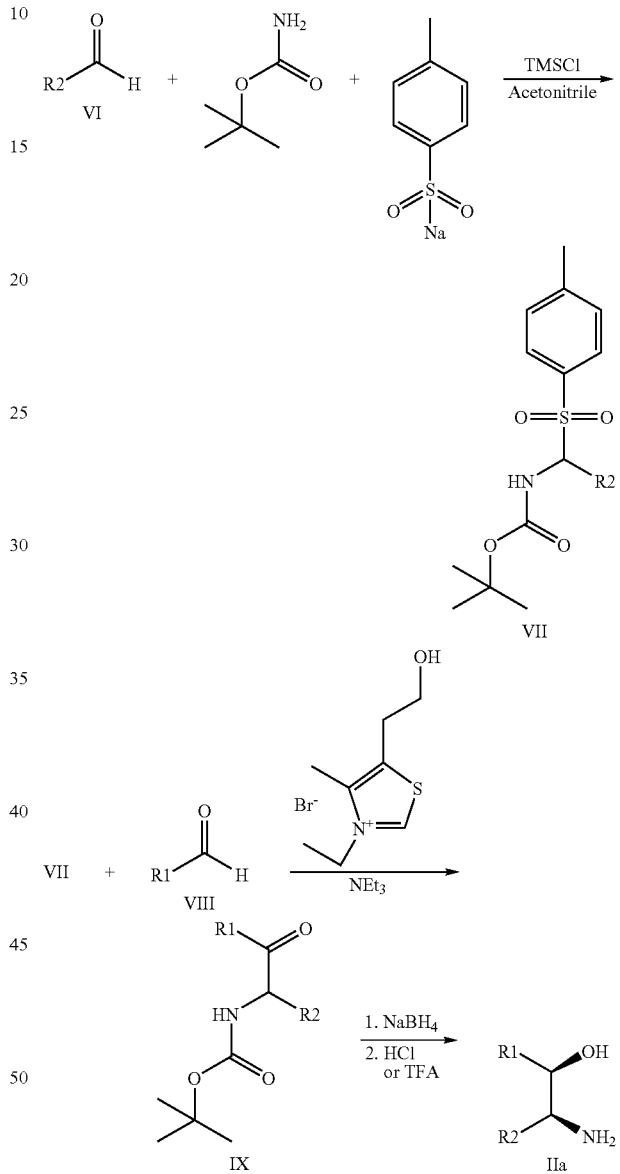

1 mole equivalent of the particular aldehyde of formula VI was added to a solution of 1.5 mole equivalents of tert-butyl carbamate and 1.5 mole equivalents of sodium p-toluenesulfonate in acetonitrile under argon. While cooling at 0-10° C., 2 mole equivalents of chlorotrimethylsilane were added dropwise, and the mixture was left to stir at room temperature overnight. After addition of 400 ml of water, the precipitated product of formula VII was filtered off with suction and dried in vacuo at 50° C. 0.9-1.0 mole equivalent of the aldehyde of formula VIII was added to 1 mole equivalent of the resulting compound of formula VII in the presence of 0.1 to 0.3 mole equivalent of 3-ethyl-5-(2-hydroxyethyl)-4-methylthiazolium bromide and 15 mole equivalents of triethylamine in methylene chloride, and the mixture was heated at 35° C. until reaction was complete (2-8 h). The resulting reaction product of formula IX was reduced with 1 mole equivalent of sodium borohydride in methanol, and the tert-butoxycarbonyl group was eliminated with hydrochloric acid or trifluoroacetic acid. The 2-amino-1,2-diarylethanol was obtained as mixture or 2 diastereomers in which the depicted diastereomer of formula IIa normally predominated, with a proportion of 70-90%.

Method A2:

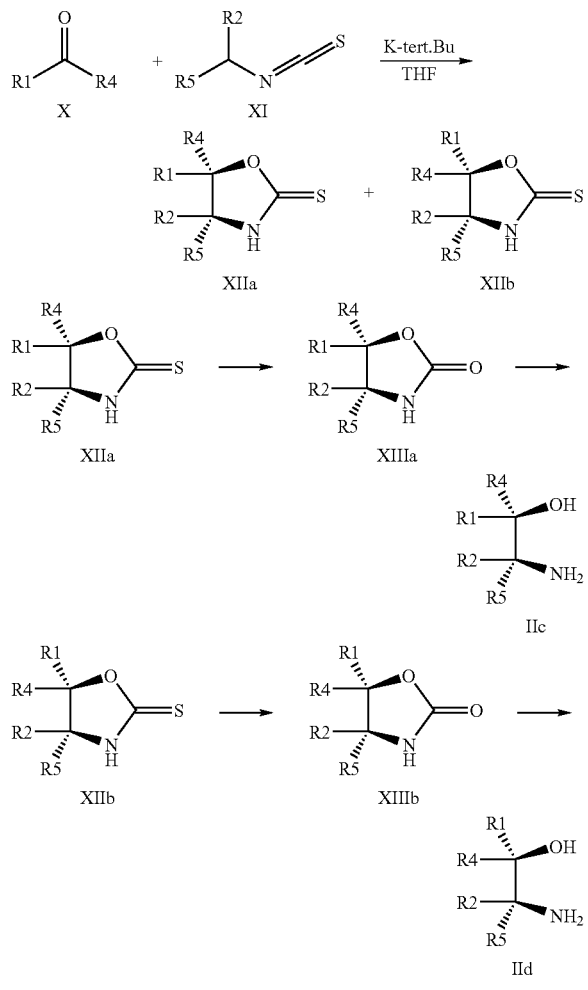

1 mole equivalent of an aldehyde or ketone of formula X and 1.2 mole equivalents of an isothiocyanate of formula XI, dissolved together in THF, were added dropwise to a solution, cooled in an ice bath, of 1.2 mole equivalents of potassium tert-butoxide in 50 ml of THF over a period of 15 minutes. After removal of the ice bath, stirring was continued for one hour and the reaction was subsequently stopped by adding dilute hydrochloric acid. The oxazolidinethiones of formula XIIa and XIIb obtained in this way could be separated where appropriate into diastereoisomers, it being possible to achieve this first by chromatographic methods and by fractional crystallization. The diastereoisomers are produced in most cases in the ratio of about 50:50. The purified oxazolidinones of formula XIIa and XIIb (for example 7 mmol) were normally dissolved in methanol and 2N sodium hydroxide solution and then treated with an excess of 35% H$_2$O$_2$. The solution became very hot and was allowed to cool to room temperature and stirred for a further 1-3 hours. After removal of most of the methanol, the resulting oxazolidinone of formula XIIIa or XIIIb resulted as crystals and could be filtered off with suction. Subsequent hydrolysis to the amino alcohols of formula IIc or IId took place under the following conditions: 1 mole equivalent of oxazolidinone of formula XIIIa or XIIIb were dissolved in ethanol, and 9 mole equivalents of KOH dissolved in H$_2$O were added. The mixture was boiled under reflux for 8 to 24 hours.

Method A3:

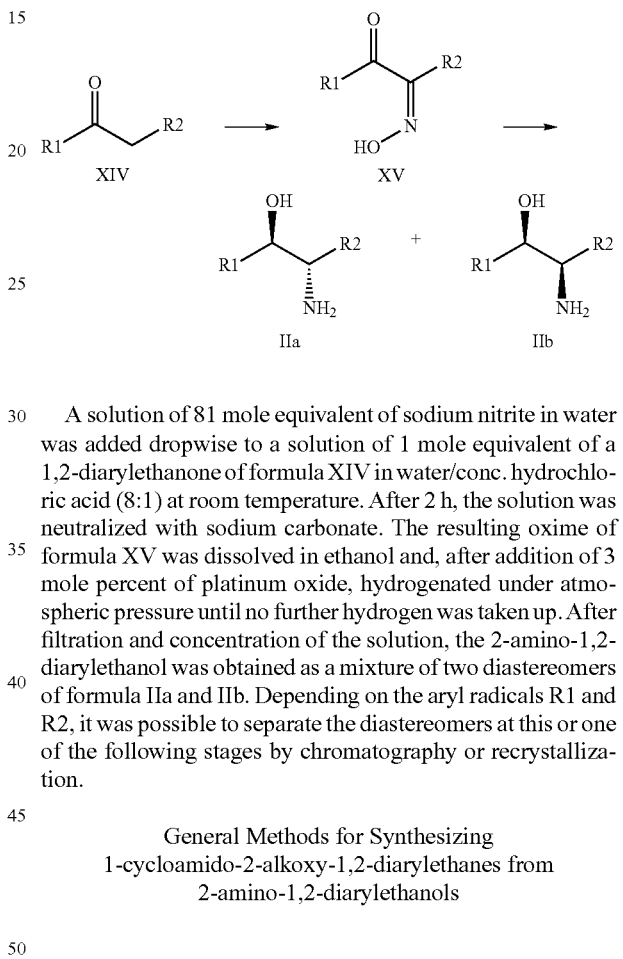

A solution of 81 mole equivalent of sodium nitrite in water was added dropwise to a solution of 1 mole equivalent of a 1,2-diarylethanone of formula XIV in water/conc. hydrochloric acid (8:1) at room temperature. After 2 h, the solution was neutralized with sodium carbonate. The resulting oxime of formula XV was dissolved in ethanol and, after addition of 3 mole percent of platinum oxide, hydrogenated under atmospheric pressure until no further hydrogen was taken up. After filtration and concentration of the solution, the 2-amino-1,2-diarylethanol was obtained as a mixture of two diastereomers of formula IIa and IIb. Depending on the aryl radicals R1 and R2, it was possible to separate the diastereomers at this or one of the following stages by chromatography or recrystallization.

General Methods for Synthesizing
1-cycloamido-2-alkoxy-1,2-diarylethanes from
2-amino-1,2-diarylethanols Method B1:

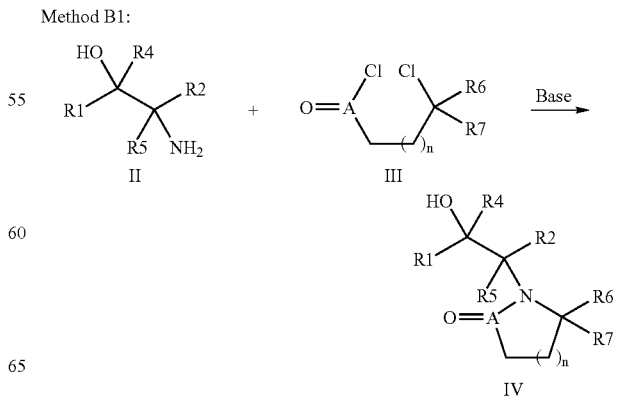

-continued

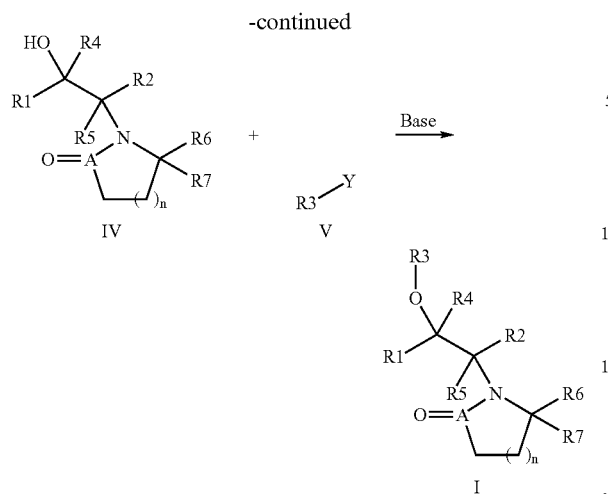

2-3 mole equivalents of triethylamine and 1 mole equivalent of an ω-haloalkylcarbonyl or sulfonyl chloride of formula III (for example 5-chlorobutyryl chloride) were slowly added dropwise to a solution of a 2-amino-1,2-diarylethanol of formula II in DMF. After stirring for 20 min, 10 mole equivalents of sodium hydroxide pellets were added at 0° C., and the mixture was stirred at room temperature for 3 h. The mixture was poured into ice-water, and the precipitated product was filtered off with suction or isolated by extraction with ethyl acetate. Subsequently the alcohol of formula IV was reacted with 1 mole equivalent of a compound of formula V where Y is preferably chlorine, bromine or iodine if R3 is an aliphatic radical, and may also be fluorine if R3 is an aromatic radical, i.e. for example with an alkyl bromide or an aryl fluorine compound such as, for example, cyclopropylmethyl bromide or p-fluorobenzonitrile. The reactions were carried out either in DMF with addition of at least 1 mole equivalent of sodium hydride or in DMSO using potassium hydroxide as base. Depending on the progress of the reaction, further amounts of the compound of formula V and base were subsequently added until complete reaction was achieved.

Method B2:

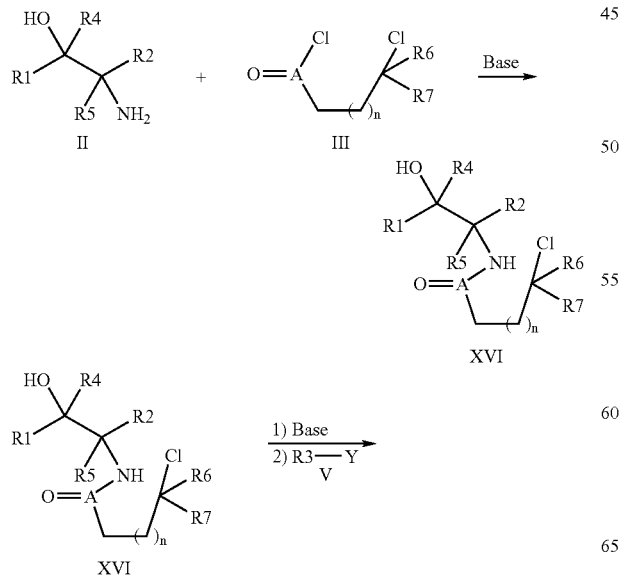

-continued

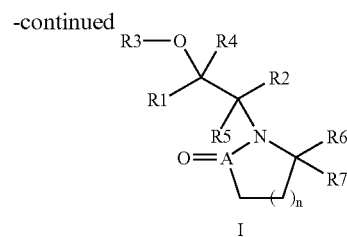

A solution of an amine alcohol of formula II or its hydrochloride was dissolved in methylene chloride, and the same volume of a saturated aqueous solution of sodium bicarbonate was introduced on top. 1.05 mole equivalents of an ω-haloalkylcarbonyl or sulfonyl chloride of formula III was added to the vigorously stirred mixture, and the mixture was stirred at room temperature for a further 60 minutes. The organic phase was then separated off, and a compound of formula XVI was isolated therefrom by crystallization. The compounds of formula XVI were dissolved in DMSO, and 10-100 mole equivalents of powdered NaOH were added. After stirring at room temperature for 10-30 minutes, 3-5 mole equivalents of a compound of formula V were added, where Y may have the meanings described for method B1. The mixture was stirred at room temperature for 1-10 hours, and further equivalents of the compound of formula V were added where appropriate, until alkylation was complete.

General Method for Synthesizing
1-cycloamido-2-alkoxy-1,2-diarylethanes from
bromo ketones Method C:

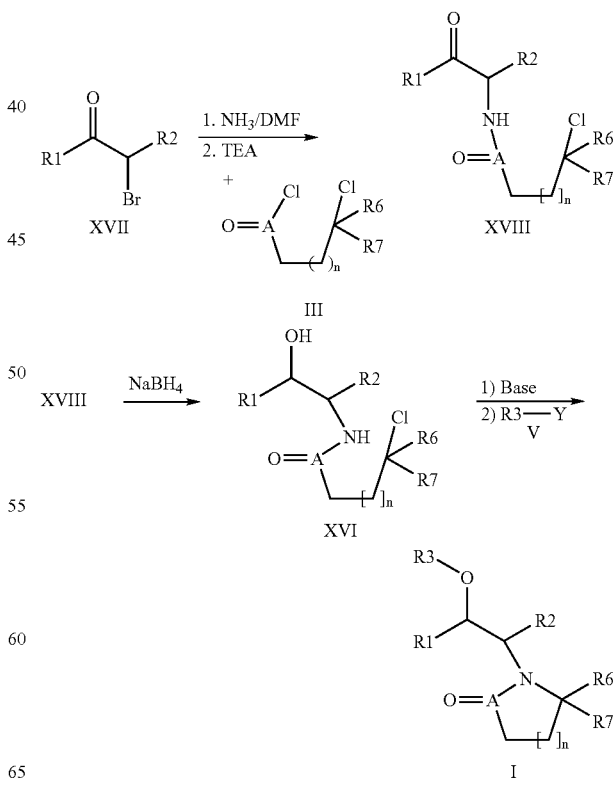

A vigorous stream of NH₃ gas was passed through a vigorously stirred solution in dimethylformamide of a bromo ketone of formula XVII substituted by R2 and R1 for 15 to 20 minutes, followed by a vigorous stream of air for 30 minutes, in order to remove excess NH₃ again from the solution. Subsequently, 1.1 mole equivalents of triethylamine and 1.1 mole equivalents of an ω-haloalkylcarbonyl or sulfonyl chloride of formula III were added to the mixture. The compound of formula XVIII which resulted in this case was isolated in a conventional way and subsequently reduced with sodium borohydride in methanol.

The amino alcohols of formula XVI obtained in this way were dissolved in DMSO, and 10-100 mole equivalents of powdered NaOH were added. After stirring at room temperature for 10-30 minutes, 3-5 mole equivalents of the compound of formula V were added, where Y may have the meanings described for method B1. The mixture was stirred at room temperature for 1-10 hours, and further equivalents of the compound of formula V were added where appropriate, until alkylation was complete.

The starting compounds described in the synthetic methods, such as the compounds of formula III, V, VI, VII, X, XI, XIV and XVII can be purchased or can be prepared by or in analogy to processes described in the literature and known to the skilled worker.

The working up and, if desired, the purification of the products and/or intermediates takes place by conventional methods such as extraction, chromatography or crystallization and conventional dryings.

EXAMPLES OF THE USE OF THE GENERAL SYNTHETIC METHODS

Example 1

1-[(1R',2S')-2-Cyclopropylmethoxy-1-(4-fluorophenyl)-2-quinolin-8-ylethyl]-piperidin-2-one (Synthesis by General Method: A1+B1)

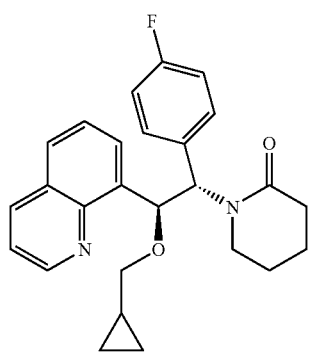

-continued

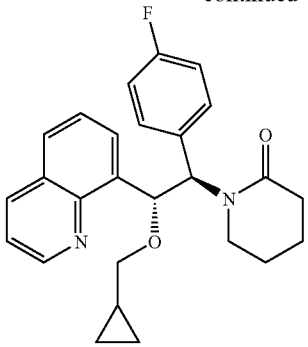

a) tert-Butyl [(4-fluorophenyl)(toluene-4-sulfonyl)methyl]carbamate 15.0 g (121 mmol) of 4-fluorobenzaldehyde were added to a solution of 21.3 g (184 mmol) of tert-butyl carbamate and 32.3 g (181 mmol) of sodium p-toluenesulfonate in 430 ml of acetonitrile under argon. While cooling to 0-10° C., 26.3 g (242 mmol) of chlorotrimethylsilane were added dropwise, and the mixture was left to stir at room temperature overnight. After addition of 400 ml of water, the precipitated product was filtered off with suction and dried in vacuo at 50° C. 36.3 g of tert-butyl [(4-fluorophenyl)(toluene-4-sulfonyl)methyl]carbamate were obtained.

b) tert-Butyl [1-(4-fluorophenyl)-2-oxo-2-quinolin-8-ylethyl]carbamate 1.9 g (5.1 mmol) of tert-butyl [(4-fluorophenyl)(toluene-4-sulfonyl)methyl]carbamate, 255 mg (1.0 mmol) of 3-ethyl-5-(2-hydroxyethyl)-4-methylthiazolium bromide, 10.5 ml (76 mmol) of triethylamine and 0.72 g (4.55 mmol) of 8-quinolinecarbaldehyde were mixed in 44 ml of methylene chloride at room temperature and then heated at 35° C. for 3 h. After reaction of the aldehyde was complete, 25 ml of saturated ammonium chloride solution were added, and the reaction mixture was stirred for 15 minutes. After removal of the aqueous phase, the organic phase was washed with 0.5 M sodium hydroxide solution and saturated sodium chloride solution, and 1.7 g of tert-butyl [1-(4-fluorophenyl)-2-oxo-2-quinolin-8-ylethyl]carbamate were obtained and were reacted further without purification.

c) 2-Amino-2-(4-fluorophenyl)-1-quinolin-8-ylethanol 0.48 g (13 mmol) of sodium borohydride was added to a solution of 4.9 g (13 mmol) of tert-butyl [1-(4-fluorophenyl)-2-oxo-2-quinolin-8-ylethyl]carbamate in 75 ml of methanol at 0-5° C. After 1 h, the reaction mixture was concentrated and diluted with ethyl acetate and water, and the organic phase was washed with saturated ammonium chloride and sodium bicarbonate solutions. The residue after drying of the organic phase and concentration was dissolved in 40 ml of methylene chloride, and 9 ml of trifluoroacetic acid were added. After 2 h, ice-water was added and the product was extracted into the aqueous phase. The aqueous phase was made alkaline, the product was extracted with methylene chloride, and 1.5 g of 2-amino-2-(4-fluorophenyl)-1-quinolin-8-ylethanol were obtained.

d) 1-[(1R',2S')-1-(4-Fluorophenyl)-2-hydroxy-2-quinolin-8-ylethyl]piperidin-2-one 0.43 g (2.7 mmol) of 5-chlorovaleryl chloride was slowly added dropwise to a solution of 0.75 g (2.7 mmol) of 2-amino-2-(4-fluorophenyl)-1-quinolin-8-ylethanol and 0.41 g (4.0 mmol) of triethylamine in 17 ml of DMF. After stirring for 20 min, 1.3 g (33 mmol) of sodium hydroxide pellets were added at 0° C., and the mixture was stirred at room temperature for 3 h. The mixture was poured into the ice-water, and the precipitated product was filtered off with suction and recrystallized from heptane/ethyl acetate. 600 mg of 1-[(1R',2S')-1-(4-fluorophenyl)-2-hydroxy-2-quinolin-8-ylethyl]piperidin-2-one were obtained as a single diastereomer.

e) 1-[(1R',2S')-2-Cyclopropylmethoxy-1-(4-fluorophenyl)-2-quinolin-8-ylethyl]piperidin-2-one 26 mg (0.55 mmol) of sodium hydride were added to a solution of 0.2 g (0.55 mmol) of 1-[(1R',2S')-1-(4-fluorophenyl)-2-hydroxy-2-quinolin-8-ylethyl]piperidin-2-one in 4 ml of DMF at −10° C. After stirring for 1 h, 222 mg (1.6 mmol) of cyclopropylmethyl bromide were added. After stirring overnight, 26 mg of sodium hydride and 222 mg of cyclopropylmethyl bromide were added on each of two further occasions until the starting material had completely reacted. The residue after concentration in vacuo was taken up in 20 ml of water and 20 ml of ethyl acetate, and the organic phase was washed with saturated sodium bicarbonate solution. Drying and concentration in vacuo resulted in 0.23 g of 1-[(1R',2S')-2-cyclopropylmethoxy-1-(4-fluorophenyl)-2-quinolin-8-ylethyl]piperidin-2-one.

Example 2

1-[(1R',2S')-1-(4-Fluorophenyl)-2-pyridin-3-yl-2-(4,4,4-trifluorobutoxy)-ethyl]pyrrolidin-2-one (synthesis by general method: A1+B1)

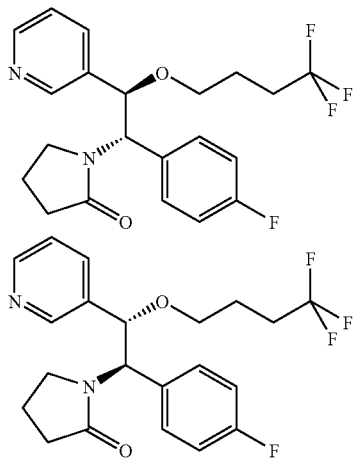

a) tert-Butyl [1-(4-fluorophenyl)-2-oxo-2-pyridin-3-ylethyl]carbamate 10.0 g (26.4 mmol) of tert-butyl [(4-fluorophenyl)(toluene-4-sulfonyl)methyl]carbamate, 665 mg (2.6 mmol) of 3-ethyl-5-(2-hydroxyethyl)-4-methylthiazolium bromide, 55 ml (395 mmol) of triethylamine and 5.6 g (26.4 mmol) of 3-pyridinecarboxaldehyde were mixed in 230 ml of methylene chloride at room temperature and then heated at 35° C. for 3 h. After reaction of the aldehyde was complete, 100 ml of saturated ammonium chloride solution were added, and the reaction mixture was stirred for 10 minutes. After removal of the aqueous phase, the organic phase was washed with 0.5 M sodium hydroxide solution and saturated sodium chloride solution. 9.7 g of tert-butyl [1-(4-fluorophenyl)-2-oxo-2-pyridin-3-ylethyl]carbamate were obtained and were reacted further without purification.

b) (1S',2R')-2-Amino-2-(4-fluorophenyl)-1-pyridin-3-ylethanol 0.36 g (9.6 mmol) of sodium borohydride was added to a solution of 3.2 g (9.6 mmol) of tert-butyl [1-(4-fluorophenyl)-2-oxo-2-pyridin-3-ylethyl]carbamate in 40 ml of methanol at 0-5° C. After 3 h, the reaction mixture was diluted with ethyl acetate and washed with water. The residue after drying of the organic phase and concentration was suspended in 60 ml of methylene chloride, and 18 ml of a saturated solution of HCl in dioxane were added. After 2 h, the precipitated product was filtered off with suction, and 1.7 g of (1S',2R')-2-amino-2-(4-fluorophenyl)-1-pyridin-3-ylethanol were obtained as hydrochloride.

c) 1-[(1R',2S')-1-(4-Fluorophenyl)-2-hydroxy-2-pyridin-3-ylethyl]pyrrolidin-2-one 0.87 g (6.1 mmol) of 5-chlorobutyl chloride was slowly added dropwise to a solution of 1.7 g (6.1 mmol) of (1S',2R')-2-amino-2-(4-fluorophenyl)-1-pyridin-3-ylethanol hydrochloride and 1.6 g (15.4 mmol) of triethylamine in 40 ml of DMF. After stirring for 30 min, 3.1 g (77 mmol) of sodium hydroxide pellets were added at 0° C., and the mixture was stirred at room temperature for 3 h. The mixture was poured into 100 ml of ice-water and extracted with ethyl acetate. After washing the organic phase with saturated ammonium chloride and saline solution, 1.57 g of 1-[(1R',2S')-1-(4-fluorophenyl)-2-hydroxy-2-pyridin-3-ylethyl]pyrrolidin-2-one were obtained.

d) 1-[(1R',2S')-1-(4-Fluorophenyl)-2-pyridin-3-yl-2-(4,4,4-trifluorobutoxy)ethyl]pyrrolidin-2-one 0.26 g (6.6 mmol) of 60 percent sodium hydride and 1.26 g (6.6 mmol) of 4,4,4-trifluorobutyl bromide were added to a solution of 1.98 g (6.6 mmol) of 1-[(1R',2S')-1-(4-fluorophenyl)-2-hydroxy-2-pyridin-3-ylethyl]pyrrolidin-2-one in 60 ml of DMF at 0° C. The mixture was left to stand at room temperature for 5 days, during which 50% of the original amount of sodium hydride and 4,4,4-trifluorobutyl bromide was again added each day. The residue after aqueous working up was purified by chromatography, and the resulting product was recrystallized from ethyl acetate and heptane. 710 mg of 1-[(1R',2S')-1-(4-fluorophenyl)-2-pyridin-3-yl-2-(4,4,4-trifluorobutoxy)ethyl]pyrrolidin-2-one were obtained.

Example 3

1-[(1R',2S')-2-Cyclopropylmethoxy-2-(4-fluorophenyl)-1-quinolin-8-ylethyl]-pyrrolidin-2-one (synthesis by general method: A1+B2)

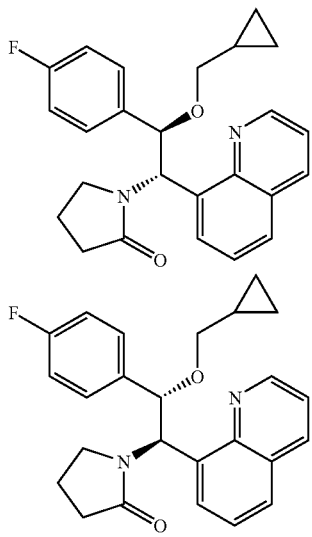

a) tert-Butyl [quinolin-8-yl(toluene-4-sulfonyl)methyl]carbamate 5.0 g (32 mmol) of 8-quinolinecarbaldehyde were added to a solution of 5.6 g (48 mmol) of tert-butyl carbamate and 8.5 g (48 mmol) of sodium p-toluenesulfonate in 112 ml of acetonitrile under argon. While cooling to 0-10° C., 6.9 g (64 mmol) of chlorotrimethylsilane were added dropwise, and the mixture was left to stir at room temperature overnight. After addition of 130 ml of water, the precipitated product was filtered off with suction and dried in vacuo at 50° C. 11.4 g of tert-butyl [quinolin-8-yl(toluene-4-sulfonyl)methyl]carbamate were obtained.

b) tert-Butyl [2-(4-fluorophenyl)-2-oxo-1-quinolin-8-ylethyl]carbamate 5.5 g (13 mmol) of tert-butyl [quinolin-8-yl(toluene-4-sulfonyl)methyl]carbamate, 336 mg (1.3 mmol) of 3-ethyl-5-(2-hydroxyethyl)-4-methylthiazolium bromide, 27 ml (200 mmol) of triethylamine and 3.9 g (13 mmol) of 4-fluorobenzaldehyde were mixed in 115 ml of methylene chloride at room temperature and then heated at 35° C. for 3 h. After reaction of the aldehyde was complete, 50 ml of saturated ammonium chloride solution were added, and the reaction mixture was stirred for 10 minutes. After removal of the aqueous phase, the organic phase was washed with 0.5 M sodium hydroxide solution and saturated sodium chloride solution. Drying of the organic phase over magnesium sulfate and concentration resulted in a semisolid residue which was stirred with 50 ml of diethyl ether. Filtration of the solid residue by suction resulted in 3.2 g of tert-butyl [2-(4-fluorophenyl)-2-oxo-1-quinolin-8-ylethyl]carbamate.

c) (1S',2R')-2-Amino-1-(4-fluorophenyl)-2-quinolin-8-ylethanol 0.30 g (7.9 mmol) of sodium borohydride was added to a solution of 3.0 g (7.9 mmol) of tert-butyl [2-(4-fluorophenyl)-2-oxo-1-quinolin-8-ylethyl]carbamate in 13 ml of methanol at 0-5° C. After 2 h, the reaction mixture was diluted with ethyl acetate and water, and the organic phase was washed with saturated ammonium chloride and sodium bicarbonate solutions. The residue after drying of the organic phase and concentration was dissolved in 30 ml of methylene chloride, and 11 ml of trifluoroacetic acid were added. After 2 h, ice-water was added and the product was extracted into the aqueous phase. After the aqueous phase had been made alkaline, the product was extracted with methylene chloride to result in 1.8 g of (1S',2R')-2-amino-1-(4-fluorophenyl)-2-quinolin-8-ylethanol.

d) (1R',2S')-4-Chloro-N-[2-(4-fluorophenyl)-2-hydroxy-1-quinolin-8-ylethyl]butyramide 0.85 g (6 mmol) of 4-chlorobutyryl chloride was added to a solution of 1.8 g (4.6 mmol) of (1S',2R')-2-amino-1-(4-fluorophenyl)-2-quinolin-8-ylethanol and 2 ml of triethylamine in 40 ml of DMF at 0° C. After the mixture had been left to stand overnight it was subjected to aqueous working up, and the reaction product was purified by chromatography with heptane/ethyl acetate 50:50 to 25:75.1.8 g of (1R',2S')-4-chloro-N-[2-(4-fluorophenyl)-2-hydroxy-1-quinolin-8-ylethyl]butyramide were obtained.

e) 1-[(1R',2S')-2-Cyclopropylmethoxy-2-(4-fluorophenyl)-1-quinolin-8-ylethyl]pyrrolidin-2-one A solution of 1.8 g of 4-chloro-N-[(1R',2S')-2-(4-fluorophenyl)-2-hydroxy-1-quinolin-8-ylethyl]butyramide, 560 mg of potassium hydroxide and 1.0 g of cyclopropylmethyl bromide in 15 ml of DMSO was stirred at room temperature overnight. The crude product obtained after aqueous working up was purified by chromatography on silica gel with heptane/ethyl acetate 50:50 to result in 0.45 g of 1-[(1R',2S')-2-cyclopropylmethoxy-2-(4-fluorophenyl)-1-quinolin-8-ylethyl]pyrrolidin-2-one.

Example 4

4-[(1R',2S')-1-(3,4-Difluorophenyl)-2-(4-fluorophenyl)-2-(2-oxopyrrolidin-1-yl)ethoxy]benzonitrile (synthesis by general method: A1+B1)

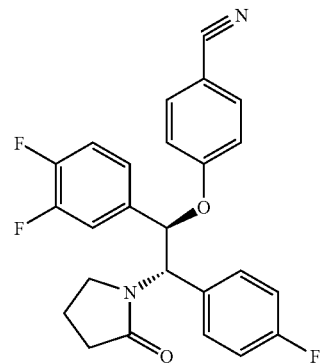

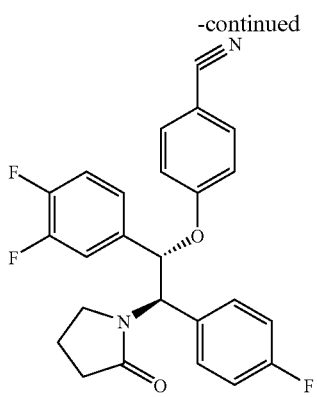

a) tert-Butyl [2-(3,4-difluorophenyl)-1-(4-fluorophenyl)-2-oxoethyl]carbamate 30.0 g (79 mmol) of tert-butyl [(4-fluorophenyl)(toluene-4-sulfonyl)methyl]carbamate, 5.9 g (23 mmol) of 3-ethyl-5-(2-hydroxyethyl)-4-methylthiazolium bromide, 164 ml (1.2 mol) of triethylamine and 11.2 g (79 mmol) of 3,4-difluorobenzaldehyde were mixed in 700 ml of methylene chloride at room temperature and then heated at 35° C. for 6 h. After reaction of the aldehyde was complete, saturated ammonium chloride solution was added, and the reaction mixture was stirred for 15 minutes. After removal of the aqueous phase, the organic phase was washed with 0.5 M sodium hydroxide solution and saturated sodium chloride solution to result in 29.0 g of tert-butyl [2-(3,4-difluorophenyl)-1-(4-fluorophenyl)-2-oxoethyl]carbamate, which was reacted further without purification.

b) tert-Butyl [(1R',2S')-2-(3,4-difluorophenyl)-1-(4-fluorophenyl)-2-hydroxyethyl]carbamate 3.0 g (79 mmol) of sodium borohydride were added in portions to a solution of 29.0 g (79 mmol) of tert-butyl [2-(3,4-difluorophenyl)-1-(4-fluorophenyl)-2-oxoethyl]carbamate in 450 ml of methanol at 5° C. After 1 h, the precipitate which had separated out was filtered off with suction to result in 23.3 g of tert-butyl [(1R',2S')-2-(3,4-difluorophenyl)-1-(4-fluorophenyl)-2-hydroxyethyl]carbamate.

c) (1S',2R')-2-Amino-1-(3,4-difluorophenyl)-2-(4-fluorophenyl)ethanol 20 ml of a saturated solution of HCl in dioxane were added to a solution of 23.3 g of tert-butyl [(1R',2S')-2-(3,4-difluorophenyl)-1-(4-fluorophenyl)-2-hydroxyethyl]carbamate in 400 ml of methylene chloride, and the mixture was left to stir at room temperature for 3 h. After cooling to 0° C., 17.0 g of the hydrochloride of (1S', 2R')-2-amino-1-(3,4-difluorophenyl)-2-(4-fluorophenyl)ethanol precipitate.

d) 1-[(1R',2S')-2-(3,4-Difluorophenyl)-1-(4-fluorophenyl)-2-hydroxyethyl]pyrrolidin-2-one 0.9 g (9.1 mmol) of triethylamine and 0.51 g (3.6 mmol) of 4-chlorobutyryl chloride were added dropwise to a solution of 1.1 g (3.6 mmol) of (1S',2R')-2-amino-1-(3,4-difluorophenyl)-2-(4-fluorophenyl)ethanol hydrochloride in 45 ml of THF at 0° C. After 1 h, 1.8 g (45 mmol) of sodium hydroxide and 10 ml of DMF were added, and stirring was continued for 1 hour. The mixture was added to ice-water, and the organic phase was washed with ammonium chloride solution and sodium chloride solution. Drying and concentration resulted in 0.89 g of 1-[(1R',2S')-2-(3,4-difluorophenyl)-1-(4-fluorophenyl)-2-hydroxyethyl]pyrrolidin-2-one.

e) 4-[(1R',2S')-1-(3,4-Difluorophenyl)-2-(4-fluorophenyl)-2-(2-oxopyrrolidin-1-yl)ethoxy]-benzonitrile 0.13 g (2.9 mmol) of sodium hydride was added to a solution of 0.89 g (2.6 mmol) of 1-[(1R',2S')-2-(3,4-difluorophenyl)-1-(4-fluorophenyl)-2-hydroxyethyl]pyrrolidin-2-one in 40 ml of DMF at 0° C. After 5 minutes, 0.32 g (2.6 mmol) of 4-fluorobenzonitrile was added, and the mixture was stirred for 2 h. Purification of the crude product by chromatography resulted in 0.69 g of 4-[(1R',2S')-1-(3,4-difluorophenyl)-2-(4-fluorophenyl)-2-(2-oxopyrrolidin-1-yl)ethoxy]benzonitrile.

Example 5

1-[(1R',2S')-2-Cyclopropylmethoxy-2-phenyl-1-pyridin-2-ylethyl]pyrrolidin-2-one (synthesis by general method: A3+B1)

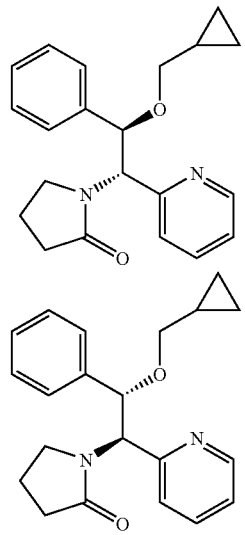

a) 1-Phenyl-2-pyridin-2-ylethane-1,2-dione 2-oxime

A solution of 8.75 g (127 mmol) of sodium nitrite in water was added dropwise to a solution of 25 g (127 mmol) of 1-phenyl-2-pyridin-2-ylethanone in 250 ml of water/conc. hydrochloric acid (8:1) at room temperature. After 2 h, the solution was neutralized with sodium carbonate. The product crystallized out overnight to result in 25.3 g of 1-phenyl-2-pyridin-2-ylethane-1,2-dione 2-oxime.

b) 2-Amino-1-phenyl-2-pyridin-2-ylethanol 25.3 g of 1-phenyl-2-pyridin-2-ylethane-1,2-dione 2-oxime were dissolved in 300 ml of ethanol and, after addition of 1.0 g of platinum oxide, hydrogenated under atmospheric pressure until no further hydrogen was taken up.

Filtration and concentration of the solution resulted in 21.6 g of 2-amino-1-phenyl-2-pyridin-2-ylethanol as mixture of 2 diastereomers.

c) Syn- and anti-1-(2-hydroxy-2-phenyl-1-pyridin-2-ylethyl)pyrrolidin-2-one 35 ml (252 mmol) of triethylamine and 11.3 ml (101 mmol) of 4-chlorobutyryl chloride were successively added dropwise to a solution of 21.6 g (101 mmol) of 2-amino-1-phenyl-2-pyridin-2-ylethanol in 50 ml of DMF at 50° C. After 1 h at room temperature, 48.4 g of sodium hydroxide were added, and the mixture was stirred at room temperature for 1 h. The reaction mixture was poured into ice-water and extracted with methylene chloride, and the organic phases were washed with water and sodium bicarbonate solution. Chromatography on silica gel with ethyl acetate/ethanol 20:1 resulted in isolation of 3.0 g each of the syn- and anti-diastereomer of 1-(2-hydroxy-2-phenyl-1-pyridin-2-ylethyl)pyrrolidin-2-one in pure form. The relative stereochemistry was assigned by X-ray spectroscopy.

d) 1-[(1R',2S')-2-Cyclopropylmethoxy-2-phenyl-1-pyridin-2-ylethyl]pyrrolidin-2-one A solution of 150 mg (0.53 mmol) of 1-[(1R',2S')-2-hydroxy-2-phenyl-1-pyridin-2-ylethyl]pyrrolidin-2-one, 86 mg (0.64 mmol) of cyclopropyl bromide and 0.69 mg of KOH in 2 ml of DMSO were stirred at room temperature for 4 h. Aqueous working up and purification by preparative HPLC resulted in 30 mg of 1-[(1R',2S')-2-cyclopropylmethoxy-2-phenyl-1-pyridin-2-ylethyl]pyrrolidin-2-one.

Example 6

(1R',2S')-1-[2-(4-Chlorophenyl)-1-phenyl-2-propoxyethyl]pyrrolidin-2-one (Synthesis by General Method C)

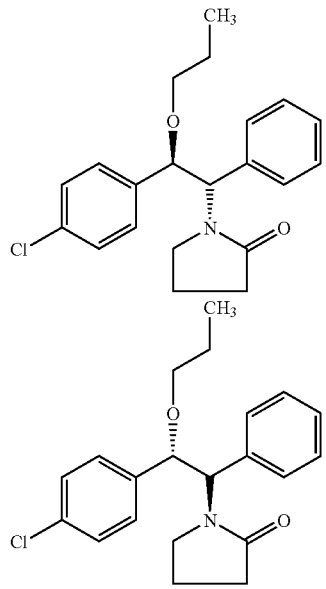

a) A vigorous stream of $NH_3$ was passed through a solution of 309 mg (1 mmol) of 2-bromo-1-(4-chlorophenyl)-2-phenylethanone for 15 minutes, and a vigorous stream of air was passed through for 20 minutes. Then 0.2 ml of triethylamine and 0.17 ml of chlorobutyryl chloride were added, and the mixture was stirred at room temperature for one hour. The solution was diluted with 80 ml of water and acidified to pH 1-2 with 2N hydrochloric acid. The DMF was stripped off in vacuo, and the aqueous residue was extracted twice with ethyl acetate. The organic phase was washed with water until neutral and dried with $MgSO_4$. The residue after evaporation of the solvent in vacuo was subjected to flash chromatography on silica gel. A heptane/ethyl acetate solvent mixture was used to elute 230 mg of the acylated amino ketone 4-chloro-N-[2-(4-chlorophenyl)-2-oxo-1-phenylethyl]butyramide.

b) The product from stage a) was dissolved in 4 ml of methanol, and 100 mg of $NaBH_4$ were added. After stirring at room temperature for 2 hours, the solvent was removed and the residue was treated with water to result in racemic (1R',2S')-4-chloro-N-[2-(4-chlorophenyl)-2-hydroxy-1-phenylethyl]butyramide in pure form.

c) 1 g of (1R',2S')-4-chloro-N-[2-(4-chlorophenyl)-2-hydroxy-1-phenylethyl]butyramide was dissolved in 20 ml of DMSO and stirred with 1 g of powdered NaOH at room temperature for 1 hour. Then 0.5 g of propyl iodide was added, and a further 0.3 g of propyl iodide was added every 45 minutes until the total amount of propyl iodide was 1.4 g. The reaction mixture was then acidified and extracted several times with ethyl acetate. The residue after evaporation of the solvent was subjected to flash chromatography on 50 g of silica gel. Heptane/ethyl acetate 7:1 eluted 670 mg of the final product (1R',2S')-1-[2-(4-chlorophenyl)-1-phenyl-2-propoxyethyl]pyrrolidin-2-one.

Example 7

(1S,2R)-2-(1,2-Diphenyl-2-propoxyethyl)isothiazolidine-1,1-dioxide (synthesis by general method B2)

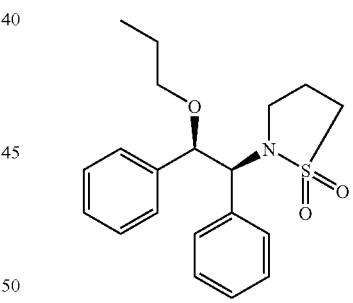

a) 213 mg (1 mmol) of (1R,2S)-(−)-2-amino-1,2-diphenylethanol were dissolved in 2 ml of DMF, and 164 µl of triethylamine (1.19 mmol) and 137 µl (1.13 mmol) of 3-chloropropanesulfonyl chloride were added. After stirring at room temperature for one hour, the reaction mixture was poured into water and filtered with suction. 310 mg (88%) of the desired intermediate 3-chloro-N-[(1S,2R)-2-hydroxy-1,2-diphenylethyl]propane-1-sulfonamide were obtained.

b) 300 mg of [(1S,2R)-2-hydroxy-1,2-diphenylethyl] amide were suspended in 8 ml of 2N sodium hydroxide solution and stirred at 80° C. for 2 hours, during which the originally crystalline suspension was converted into an oily suspension. The mixture was allowed to cool and was acidified with the minimum amount of concentrated hydrochloric acid (pH 1-2). This resulted in a crystalline precipitate of (1R,2S)-2-(1,1-dioxoisothiazolidin-2-yl)-1,2-diphenyletha-nol), which was filtered off with suction (70 mg, 0.221 mmol).

c) The product obtained from stage b) (70 mg, 0.221 mmol) was dissolved in 1 ml of DMSO, and 110 mg of powdered NaOH and then 169 mg (0.995 mmol) of n-propyl iodide were added. The reaction mixture was stirred at room temperature for 1.5 hours and then diluted with water. The crystalline precipitate obtained thereby was filtered off with suction. After drying, the material was stirred several times with n-heptane. 14.5 mg of (1S,2R)-2-(1,2-diphenyl-2-propoxy-ethyl)isothiazolidine 1,1-dioxide were obtained.

Example 8

1-(2-Cyclopropylmethoxy-1,2-diphenylpropyl)pyrro-lidin-2-one (synthesis by general method A2+B2)

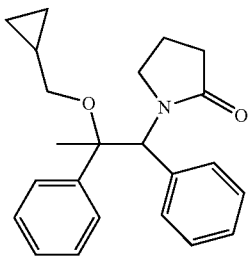

a) 2.63 g of potassium tert-butoxide (24 mmol) were dissolved in 50 ml of THF and cooled in an ice bath. A mixture of 3.918 g (24 mmol) of alpha-methylbenzyl isothiocyanate and 2.123 g (20 mmol) of benzaldehyde was added dropwise to the stirred solution over the course of 20 minutes. After addition of the reagents, the ice bath was removed and the mixture was stirred for one hour. The mixture was added to ice-water, acidified with 2N HCl and extracted 3 times with diethyl ether. The residue was prepurified by chromatography on silica gel. 1.1 g of each of the crude diastereoisomeric oxazolidinethiones were obtained. The isomer which migrated faster was isolated in pure form, 0.78 g, by trituration with diisopropyl ether. Only this isomer was subjected to the subsequent reactions.

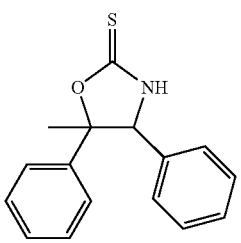

b) 0.74 g (2.75 mmol) of the oxazolidinethione obtained in stage a) was treated in 15 ml of methanol with 2N sodium hydroxide solution (7.5 ml) and 2.5 ml of 35% strength $H_2O_2$. The mixture was added to ice-water, and the product was filtered off with suction and immediately dissolved with KOH (1.1 g in 18.75 ml H2O) in 37 ml of methanol and boiled under reflux for 10 hours. The solvent was then evaporated off, the residue was diluted with water, and the resulting precipitate (1-amino-1,2-diphenyl-propan-2-ol, 470 mg) was filtered off with suction.

c) 330 mg (1.452 mmol) of 1-amino-1,2-diphenylpropan-2-ol were acylated in 3.5 ml of DMF with 215 mg (1.525 mmol) of 4-chlorobutyryl chloride and triethylamine (154 mg, 1.525 mmol) in the usual way to result in 430 mg (89%) of the corresponding chlorobutyramide.

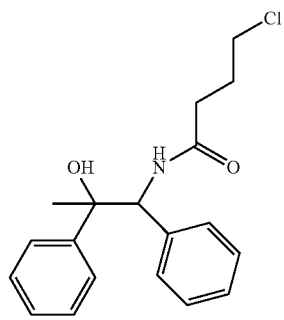

d) 420 mg (1.266 mmol) of the chlorobutyramide obtained in stage c) were dissolved in 4 ml of DMSO, and 400 mg of powdered NaOH were added. Stirring for one hour was followed by working up in the usual way, and the mixture was purified on silica gel using the eluant ethyl acetate/n-heptane 1:2. The ring-closed compound was obtained (350 mg, 94%).

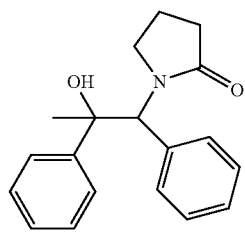

e) 210 mg of the ring-closed product (0.711 mmol) obtained in stage d) were dissolved in 2.5 ml of DMSO and stirred with 227 mg of powdered NaOH and 239 mg (1.774 mmol) of bromomethylcyclopropane at room temperature for 4 hours. The usual working up was followed by chromatography on silica gel. Using ethyl acetate/n-heptane, the 1-(2-cyclopropylmethoxy-1,2-diphenylpropyl)pyrrolidin-2-one was obtained in pure form (18 mg, 9%).

Example 9

4-[(1S',2R')-2-(4-Fluorophenyl)-2-(2-oxopyrrolidin-1-yl)-1-quinolin-8-ylethoxy]benzonitrile (synthesis by general method: A1+B1)

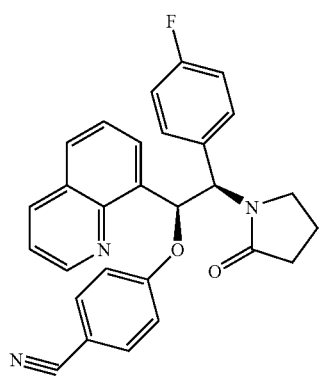

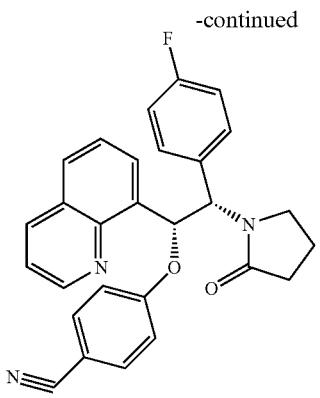

and Example 10: 4-[(1R',2R')-2-(4-Fluorophenyl)-2-(2-oxopyrrolidin-1-yl)-1-quinolin-8-ylethoxy]benzonitrile (synthesis by general method: A1+B1)

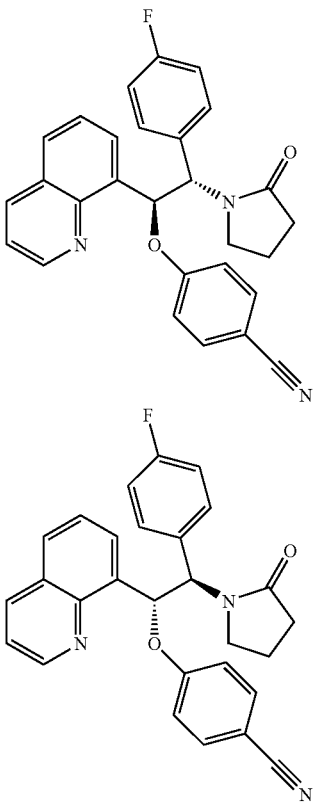

a) tert-Butyl 4[1-(4-fluorophenyl)-2-hydroxy-2-quinolin-8-ylethyl]carbamate 0.314 g (8.3 mmol) of sodium borohydride was added in 4 portions to a solution of 3.16 g (8.3 mmol) of tert-butyl [1-(4-fluorophenyl)-2-oxo-2-quinolin-8-ylethyl]carbamate in 45 ml of methanol at 0-5° C. The reaction mixture was stirred at 0-5° C. for 0.5 h and then at room temperature for 0.5 h and subsequently poured into an aqueous sodium dihydrogen phosphate solution (80 g/l). Extraction twice with ethyl acetate was followed by drying on magnesium sulfate. Concentration resulted in 2.78 g of tert-butyl [1-(4-fluorophenyl)-2-hydroxy-2-quinolin-8-ylethyl] carbamate (diastereoisomer mixture: 80/20) as pale yellow powder (yield: 88%).

b) 2-Amino-2-(4-fluorophenyl)-1-quinolin-8-yletha-nolhydrochloride 2.78 g (7.27 mmol) of tert-butyl [1-(4-fluorophenyl)-2-hydroxy-2-quinolin-8-ylethyl]carbamate were dissolved in 75 ml of methylene chloride and cooled to 0° C. 18 ml of an HCl solution (4N) in dioxane were added, and the mixture was stirred at 0° C. for 20 minutes and allowed to reach room temperature overnight. The reaction mixture was concentrated in vacuo, and the residue was treated with diisopropyl ether. Filtration was followed by washing with diisopropyl ether and pentane and drying in vacuo. 2.75 g of 2-amino-2-(4-fluorophenyl)-1-quinolin-8-ylethanol were obtained as hydrochloride (diastereoisomer mixture: 85/15) as a pale yellow very hygroscopic powder (yield: quantitative). The substance was used without further purification for the next stage.

c) 1-[1-(4-Fluorophenyl)-2-hydroxy-2-quinolin-8-ylethyl]pyrrolidin-2-one 0.615 ml (5.18 mmol) of 4-chlorobutyryl chloride (95%) was slowly added dropwise to a solution of 1.5 g (4.7 mmol) of 2-amino-2-(4-fluorophenyl)-1-quinolin-8-ylethanol hydrochloride and 1.96 ml (14.1 mmol) of triethylamine in 15 ml of DMF cooled to –8° C. After stirring at –8 to –10° C. for 1 h, 2.25 g (56.3 mmol) of sodium hydroxide pellets and 156 mg (0.94 mmol) of potassium iodide were added, and the mixture was stirred at room temperature for 3 h. The mixture was poured into an aqueous sodium dihydrogen phosphate solution (80 g/l). Extraction twice with diisopropyl ether was followed by drying over magnesium sulfate. The residue after concentration in vacuo was purified by chromatography with petroleum benzene/ethyl acetate 50:50, then 30:70 to 0:100. 845 mg of 1-[1-(4-fluorophenyl)-2-hydroxy-2-quinolin-8-yl-ethyl]pyrrolidin-2-one (diastereoisomer A) (yield: 51%) and 127 mg of 1-[1-(4-fluorophenyl)-2-hydroxy-2-quinolin-8-yl-ethyl]pyrrolidin-2-one (diastereomer B) (yield: 8%) were obtained.

Diastereomer A: 1-[(1S',2R')-1-(4-fluorophenyl)-2-hydroxy-2-quinolin-8-ylethyl]pyrrolidin-2-one Melting point: 156° C.

Diastereomer B: 1-[(1R',2R')-1-(4-fluorophenyl)-2-hydroxy-2-quinolin-8-ylethyl]pyrrolidin-2-one Melting point: pale yellow oil e) 4-[(1S',2R')-2-(4-Fluorophenyl)-2-(2-oxopyrrolidin-1-yl)-1-quinolin-8-ylethoxy]benzonitrile (Example 9)

41 mg (0.86 mmol) of sodium hydride (50% in oil) were added to a solution of 200 mg (0.57 mmol) of 1-[1-(4-fluorophenyl)-2-hydroxy-2-quinolin-8-ylethyl]pyrrolidin-2-one (diastereoisomer A) in 2 ml of DMF under argon at 0° C. After 5 minutes, 104 mg (0.86 mmol) of 4-fluorobenzonitrile were added, and the mixture was stirred at room temperature for 4 h. The reaction mixture was poured into an aqueous sodium dihydrogen phosphate solution (80 g/l) and extracted twice with diisopropyl ether. Drying over magnesium sulfate was followed by concentration. Purification of the residue by chromatography with heptane/ethyl acetate 30:70 resulted in 239 mg of 4-[(1S',2R')-2-(4-fluorophenyl)-2-(2-oxopyrrolidin-1-yl)-1-quinolin-8-ylethoxy]benzonitrile (yield: 93%) were obtained as a white powder.

Melting point: 112° C.

f) 4-[(1R',2R')-2-(4-Fluorophenyl)-2-(2-oxopyrrolidin-1-yl)-1-quinolin-8-ylethoxy]benzonitrile (Example 10)

47 mg (0.98 mmol) of sodium hydride (50% in oil) were added to a solution of 228 mg (0.65 mmol) of 1-[1-(4-fluorophenyl)-2-hydroxy-2-quinolin-8-ylethyl]pyrrolidin-2-one (diastereoisomer B) in 2 ml of DMF under argon at 0° C. After 5 minutes, 118 mg (0.97 mmol) of 4-fluorobenzonitrile were added and stirred at room temperature for 2 h. The reaction mixture was poured into an aqueous sodium dihydrogen phosphate solution (80 g/l) and extracted twice with diisopropyl ether. Drying over magnesium sulfate was followed by concentration. Purification of the residue by chromatography with heptane/ethyl acetate 30:70 resulted in 197 mg of 4-[(1R',2R')-2-(4-fluorophenyl)-2-(2-oxopyrrolidin-1-yl)-1-quinolin-8-ylethoxy]benzonitrile (diastereoisomer B) (yield: 67%).

Melting point: 188° C.

Example 11

1-[(1S',2R')-2-Cyclopropylmethoxy-1-(4-fluorophenyl)-2-naphthalen-1-ylethyl]pyrrolidin-2-one (synthesis by general method: A1+B1)

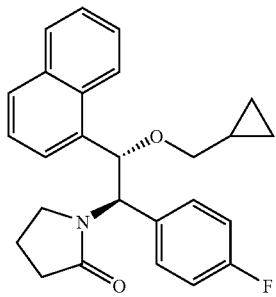

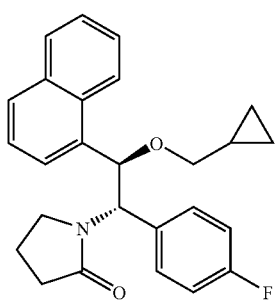

and Example 12: 1-[(1R',2R')-2-Cyclopropylmethoxy-1-(4-fluorophenyl)-2-naphthalen-1-ylethyl]pyrrolidin-2-one (synthesis by general method: A1+B1)

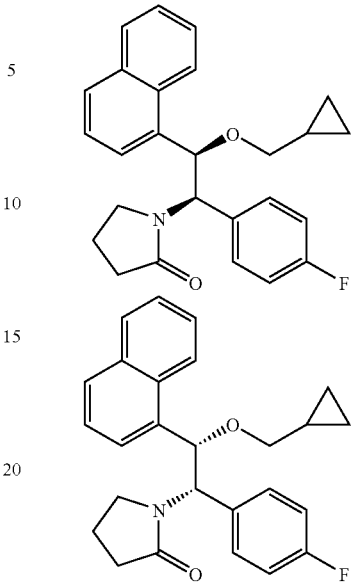

a) tert-Butyl [1-(4-fluorophenyl)-2-hydroxy-2-naphthalen-1-ylethyl]carbamate 0.72 g (18.9 mmol) of sodium borohydride was added in 4 portions to a solution of 7.2 g (18.9 mmol) of tert-butyl [1-(4-fluorophenyl)-2-naphthalen-1-yl-2-oxoethyl]carbamate in 75 ml of methanol at 0-5° C. The reaction mixture was stirred at 0-5° C. for 1 h and then poured into an aqueous sodium dihydrogen phosphate solution (80 g/l). Extraction twice with ethyl acetate was followed by drying on magnesium sulfate. Concentration resulted in 7.4 g of tert-butyl [1-(4-fluorophenyl)-2-hydroxy-2-naphthalen-1-ylethyl]carbamate (diastereoisomer mixture: 85/15) as a pale yellow oil (yield: quantitative). The substance was used without further purification for the next stage.

b) 2-Amino-2-(4-fluorophenyl)-1-naphthalen-1-ylethanol hydrochloride 7.2 g (18.9 mmol) of tert-butyl [1-(4-fluorophenyl)-2-hydroxy-2-naphthalen-1-ylethyl]carbamate were dissolved in 185 ml of methylene chloride and cooled to 0° C. 47 ml of an HCl solution (4N) in dioxane were added, and the mixture was stirred at 0° C. for 15 minutes and allowed to reach room temperature overnight. The reaction mixture was concentrated in vacuo, and the residue was treated with diisopropyl ether. Filtration was followed by washing with diisopropyl ether and pentane and drying in vacuo. 5.5 g of 2-amino-2-(4-fluorophenyl)-1-naphthalen-1-yl)ethanol were obtained as hydrochloride (diastereoisomer mixture: 85/15) as a white very hygroscopic powder (yield: 91%). The substance was used without further purification for the next stage.

c) 1-[1-(4-Fluorophenyl)-2-hydroxy-2-naphthalen-1-ylethyl]pyrrolidin-2-one 2.15 ml (18.1 mmol) of 4-chlorobutyryl chloride (95%) were slowly added dropwise to a solution of 5.5 g (17.3 mmol) of 2-amino-2-(4-fluorophenyl)-1-naphthalen-1-ylethanol hydrochloride and 7.2 ml (51.7 mmol) of triethylamine in 55 ml of DMF cooled to −10° C. After stirring at room temperature for 2.5 h, 8.3 g (208 mmol) of sodium hydroxide pellets and 862 mg (5.2 mmol) of potassium iodide were added, and the mixture was stirred at room temperature overnight. The mixture was poured into an aqueous sodium dihydrogen phosphate solution (80 g/l). Extraction twice with diisopropyl ether was followed by drying over magnesium sulfate. The residue after concentration in vacuo was purified by chromatography with petroleum benzene/ethyl acetate 50:50. 3.8 g of 1-[1-(4-fluorophenyl)-2-hydroxy-2-naphthalen-1-ylethyl]pyrrolidin-2-one (diastereoisomer A) (yield: 63%) and 728 mg of 1-[1-(4-fluorophenyl)-2-hydroxy-2-(1-naphthyl)ethyl]pyrrolidin-2-one (diastereomer B) (yield: 12%) were obtained.

Diastereomer A: 1-[(1S',2R')-1-(4-fluorophenyl)-2-hydroxy-2-naphthalen-1-ylethyl]pyrrolidin-2-one Melting point: 160° C.

Diastereomer B: 1-[(1R',2R')-1-(4-fluorophenyl)-2-hydroxy-2-naphthalen-1-ylethyl]pyrrolidin-2-one Melting point: 190° C.

d) 1-[(1S',2R')-2-Cyclopropylmethoxy-1-(4-fluorophenyl)-2-naphthalen-1-ylethyl]pyrrolidin-2-one (Example 11)

124 mg (2.58 mmol) of sodium hydride (50% in oil) were added to a solution of 800 mg (2.28 mmol) of 1-[1-(4-fluorophenyl)-2-hydroxy-2-naphthalen-1-ylethyl]pyrrolidin-2-one (diastereoisomer A) in 8 ml of DMF at 0° C. After stirring for 5 minutes, 335 µl (3.42 mmol) of cyclopropylmethyl bromide were added. After stirring at room temperature for 2 h, the mixture was poured into an aqueous sodium dihydrogen phosphate solution (80 g/l). Extraction twice with diisopropyl ether was followed by drying over magnesium sulfate. The residue after concentration in vacuo was purified by chromatography with petroleum benzene/ethyl acetate 70:30.835 mg of 1-[(1S',2R')-2-cyclopropylmethoxy-1-(4-fluorophenyl)-2-naphthalen-1-ylethyl]pyrrolidin-2-one were obtained as a white powder (yield: 90%).

Melting point: 126° C.

e) 1-[(1R',2R')-2-Cyclopropylmethoxy-1-(4-fluorophenyl)-2-naphthalen-1-ylethyl]pyrrolidin-2-one (Example 12)

149 mg (3.1 mmol) of sodium hydride (50% in oil) were added to a solution of 725 mg (2.07 mmol) of 1-[1-(4-fluorophenyl)-2-hydroxy-2-naphthalen-1-ylethyl]pyrrolidin-2-one (diastereoisomer B) in 7 ml of DMF at 0° C. After stirring for 5 minutes, 300 µl (3.1 mmol) of cyclopropylmethyl bromide were added. After stirring at room temperature for 2 h, the mixture was poured into an aqueous sodium dihydrogen phosphate solution (80 g/l). Extraction twice with diisopropyl ether was followed by drying over magnesium sulfate. The residue after concentration in vacuo was purified by chromatography with petroleum benzene/ethyl acetate 60:40. 715 mg of 1-[(1R',2R')-2-cyclopropylmethoxy-1-(4-fluorophenyl)-2-naphthalen-1-ylethyl]pyrrolidin-2-one were obtained as a white powder (yield: 85%).

Melting point: 150° C.

Example 32

1S,2R-1-(Cyclopropoxy-1,2-diphenylethyl)pyrrolidin-2-one

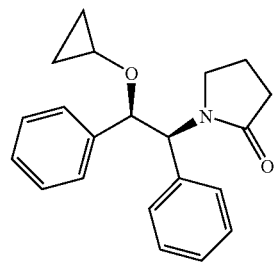

39 mg (0.127 mmol) of 1S,2R-1-(1,2-diphenyl-2-vinyloxyethyl)pyrrolidin-2-one (Example 120) were dissolved in 2 ml of absolute methylene chloride under argon. A solution of 0.63 ml (0.69 mmol) of a 1.1 molar solution of diethylzinc in toluene and then 169 mg (0.63 mmol) of methylene iodide were added thereto. The mixture was stirred at room temperature for 3 hours. The mixture was diluted with 2N hydrochloric acid and extracted with ethyl acetate. The solution dried over magnesium sulfate was evaporated in vacuo, and the residue was chromatographed with heptane/ethyl acetate 6:4 on 20 g of silica gel. 34 mg (83%) of 1S,2R-1-(cyclopropoxy-1,2-diphenylethyl)pyrrolidin-2-one were obtained.

Example 120

1 S,2R-1-(1,2-Diphenyl-2-vinyloxyethyl)pyrrolidin-2-one

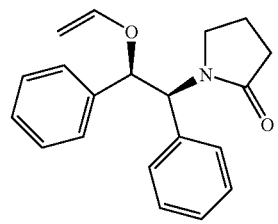

84 mg (0.3 mmol) of 1S,2R-1-(2-hydroxy-1,2-diphenylethyl)pyrrolidin-2-one plus 5 mg (0.015 mmol) of 4,7-diphenyl[1,9]phenanthroline and 5 mg (0.015 mmol) of palladium bistrifluoroacetate were dissolved in 1 ml of butyl vinyl ether and then, under argon, 9 mg (0.09 mmol) of triethylamine were added. The mixture was stirred under argon at 70° C. for 3 hours. The mixture was then poured into water and extracted several times with ethyl acetate. The combined organic phases were washed with water until neutral and dried with magnesium sulfate, and then the solvent was evaporated in vacuo. The residue was chromatographed on 20 g of silica gel with n-heptane/ethyl acetate as eluant. 1S,2R-1-(1,2-Diphenyl-2-vinyloxyethyl)pyrrolidin-2-one was obtained, 25 mg (27%).

The following examples were prepared in analogy to the synthetic methods described above:

| Example No. | Structure | Synthesis by general method: |
|---|---|---|
| 1 | | A1 + B1 |
| 2 | | A1 + B1 |
| 3 | | A1 + B2 |
| 4 | | A1 + B1 |
| 5 | | A3 + B1 |

-continued

| Example No. | Structure | Synthesis by general method: |
|---|---|---|
| 6 | 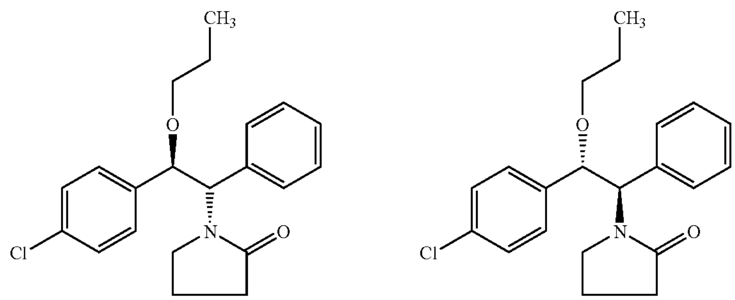 | C |
| 7 | 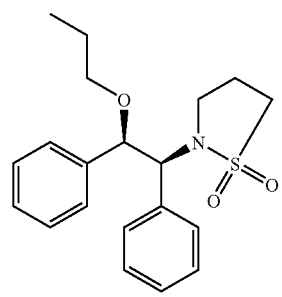 | B2 |
| 8 | 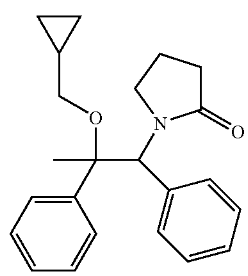 | A2 + B2 |
| 9 | 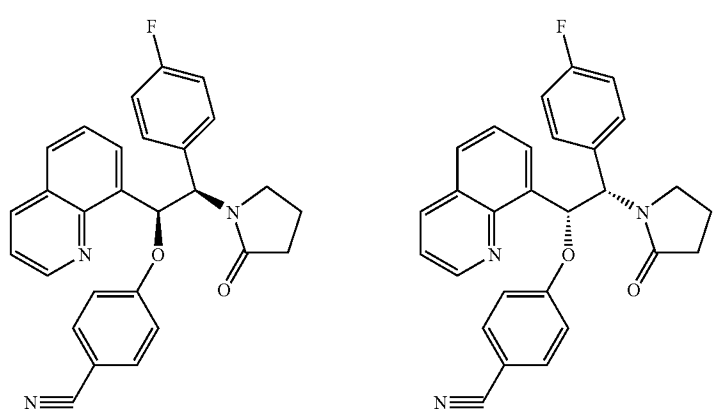 | A1 + B1 |

-continued

| Example No. | Structure | Synthesis by general method: |
|---|---|---|
| 10 | | A1 + B1 |
| 11 | | A1 + B1 |
| 12 | | A1 + B1 |
| 13 | | C |

-continued

| Example No. | Structure | Synthesis by general method: |
|---|---|---|
| 14 | | A1 + B1 |
| 15 | 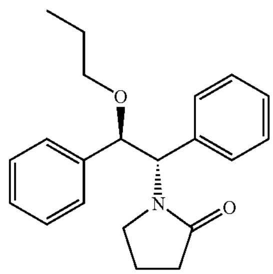 | B2 |
| 16 | | A1 + B1 |
| 17 | | A1 + B1 |
| 18 | 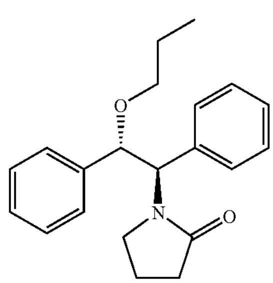 | B2 |

-continued

| Example No. | Structure | Synthesis by general method: |
|---|---|---|
| 19 | 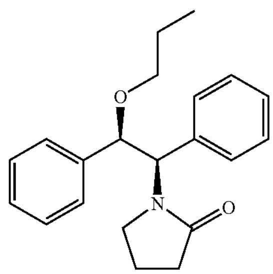 | A2 + B2 |
| 20 | 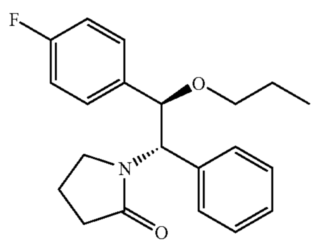 | A1 + B1 |
| 21 | 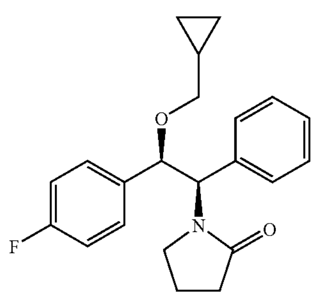 | A2 + B2 |
| 22 | 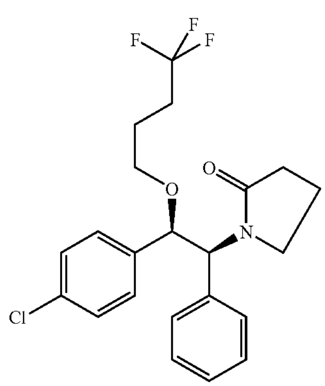 | C |
| 23 | 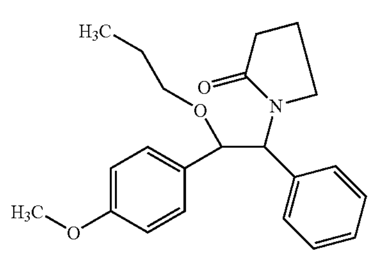 | C |

-continued

| Example No. | Structure | Synthesis by general method: |
|---|---|---|
| 24 | | A1 + B1 |
| 25 | | A2 + B2 |
| 26 | | A1 + B1 |
| 27 | | A2 + B2 |
| 28 | | A2 + B2 |

-continued

| Example No. | Structure | Synthesis by general method: |
|---|---|---|
| 29 | 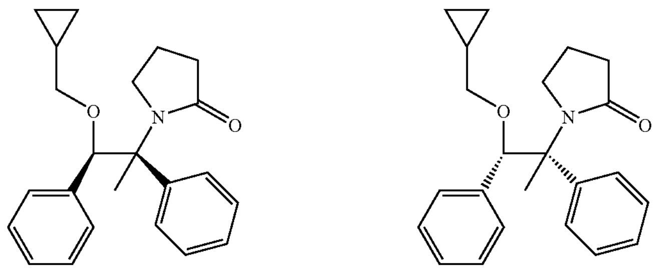 | A2 + B2 |
| 30 | 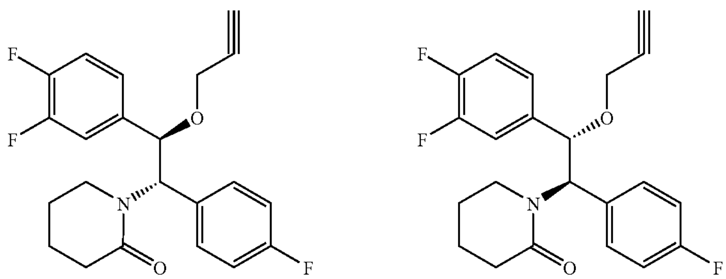 | A1 + B1 |
| 31 | 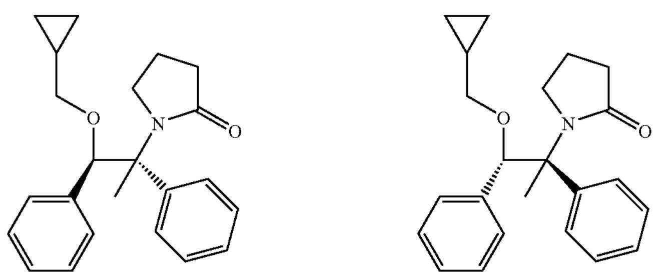 | A2 + B2 |
| 32 | 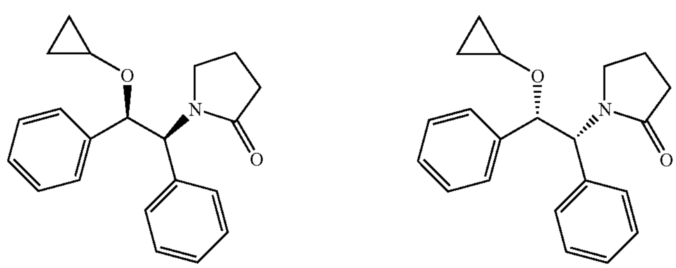 | as described above |
| 33 | 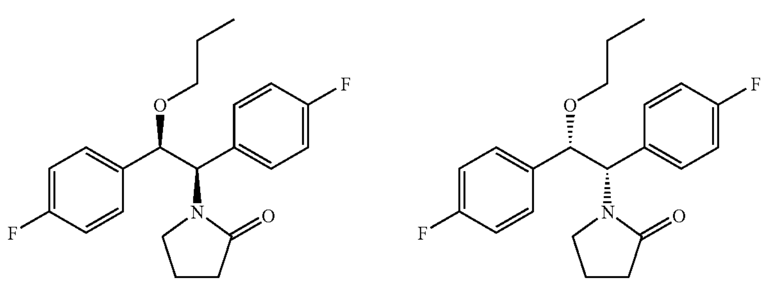 | A2 + B2 |

-continued

| Example No. | Structure | Synthesis by general method: |
|---|---|---|
| 34 | 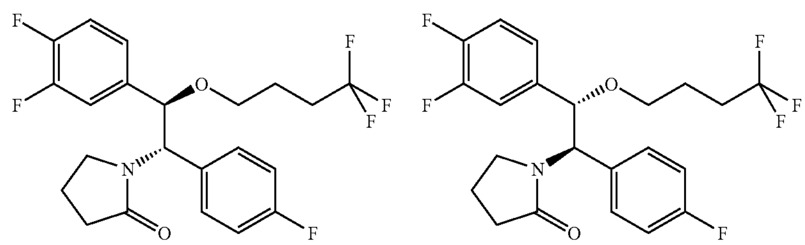 | A1 + B1 |
| 35 | 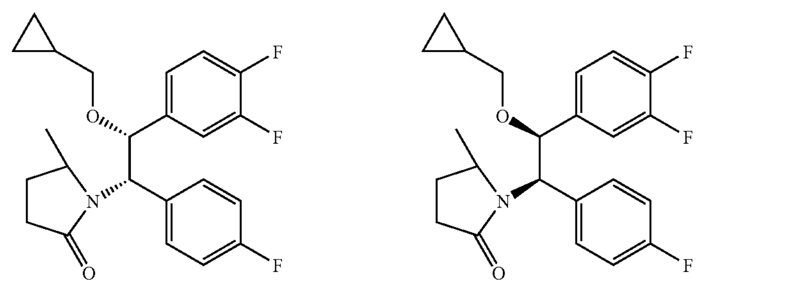 | A1 + B1 |
| 36 | 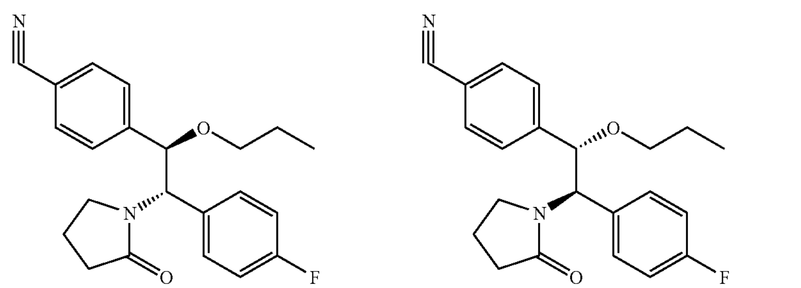 | A1 + B1 |
| 37 | 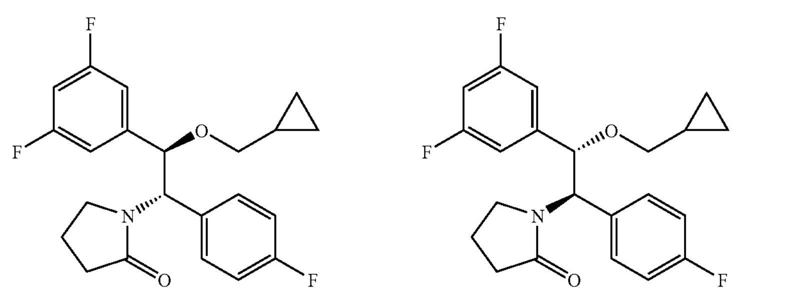 | A1 + B1 |
| 38 | 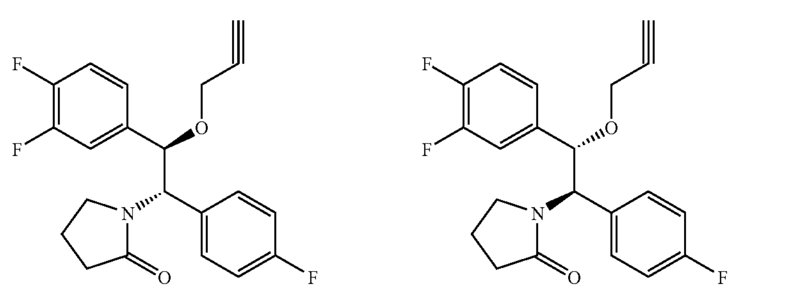 | A1 + B1 |

-continued

| Example No. | Structure | Synthesis by general method: |
|---|---|---|
| 39 | | A1 + B1 |
| 40 | | C |
| 41 | | A1 + B1 |
| 42 | | A1 + B1 |

-continued

| Example No. | Structure | | Synthesis by general method: |
|---|---|---|---|
| 43 | | | A2 + B2 |
| 44 | | | A1 + B1 |
| 45 | | | C |
| 46 | | | C |
| 47 | | | C |

| Example No. | Structure | Synthesis by general method: |
|---|---|---|
| 48 | | A1 + B1 |
| 49 | | analogous to Example 32 |
| 50 | | A1 + B1 |
| 51 | | A1 + B1 |
| 52 | 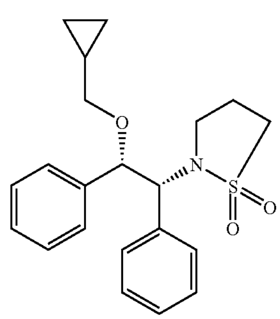 | B2 |

-continued
| Example No. | Structure | Synthesis by general method: |
|---|---|---|
| 53 | 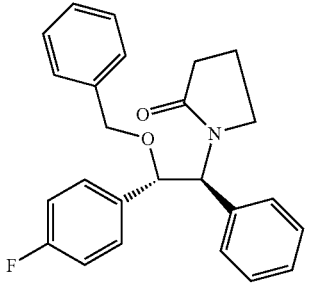 | A2 + B2 |
| 54 | 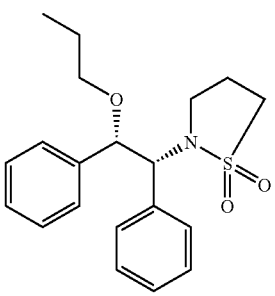 | B2 |
| 55 | 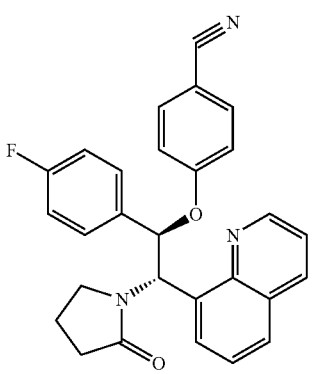 | A1 + B1 |
| 56 | 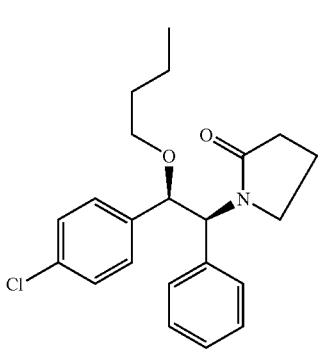 | C |

-continued

| Example No. | Structure | | Synthesis by general method: |
|---|---|---|---|
| 57 | | | C |
| 58 | | | A1 + B1 |
| 59 | | | C |
| 60 | | | C |

-continued

| Example No. | Structure | | Synthesis by general method: |
|---|---|---|---|
| 61 | | | A1 + B1 |
| 62 | | | A1 + B1 |
| 63 | | | A3 + B1 |
| 64 | | | A3 + B1 |
| 65 | | | A1 + B1 |

-continued

| Example No. | Structure | Synthesis by general method: |
|---|---|---|
| 66 | | A1 + B1 |
| 67 | | C |
| 68 | | C |
| 69 | | A1 + B1 |

-continued

| Example No. | Structure | Synthesis by general method: |
|---|---|---|
| 70 | | B1 |
| 71 | | A3 + B1 |
| 72 | | C |
| 73 | | C |

| Example No. | Structure | Synthesis by general method: |
|---|---|---|
| 74 | 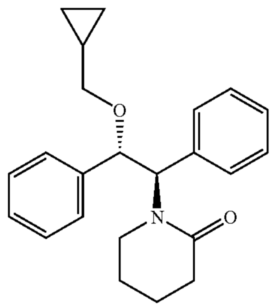 | B2 |
| 75 | 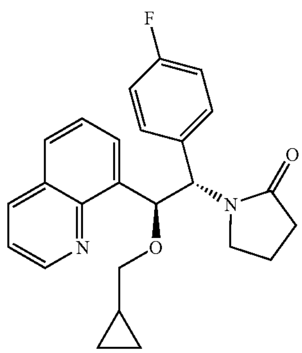 | A1 + B1 |
| 76 | 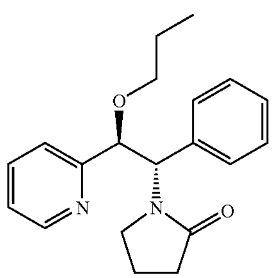 | A3 + B1 |
| 77 | 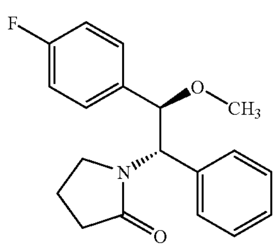 | A1 + B1 |
| 78 | 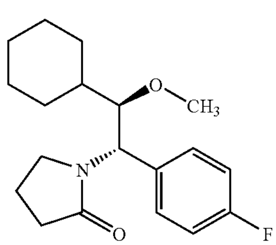 | A1 + B1 |

-continued

| Example No. | Structure | Synthesis by general method: |
|---|---|---|
| 79 | 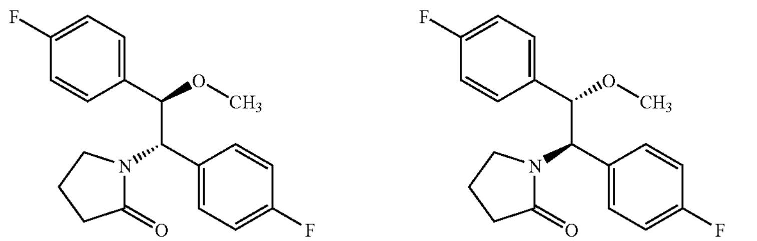 | A1 + B1 |
| 80 | 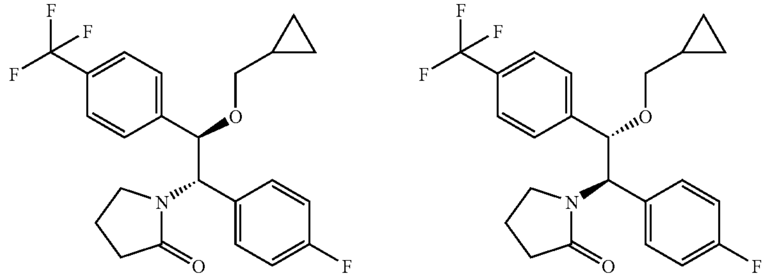 | A1 + B1 |
| 81 | 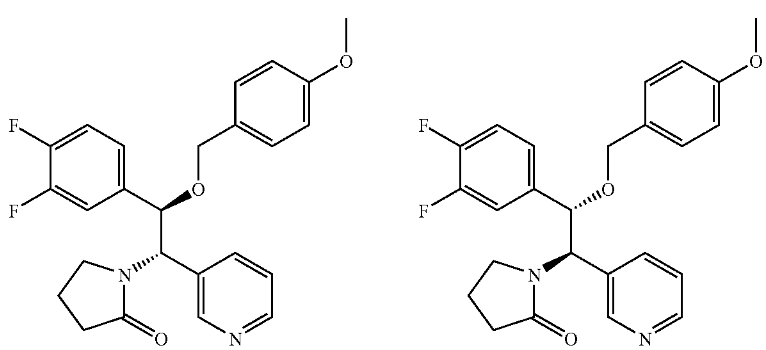 | A1 + B1 |
| 82 | 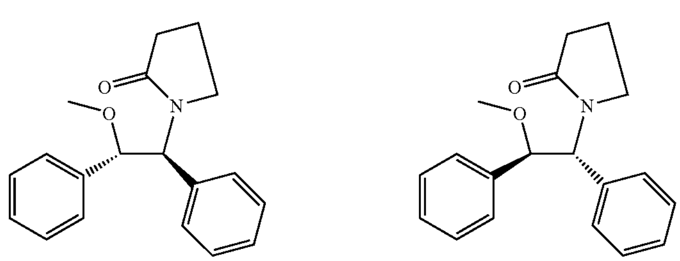 | B2 |
| 83 | 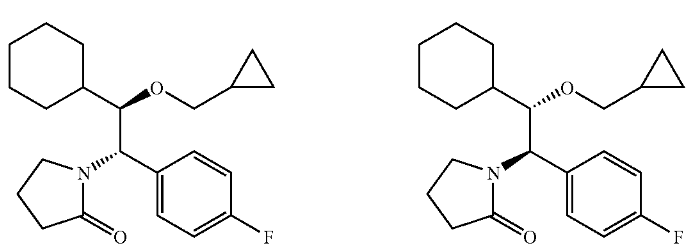 | A1 + B1 |

| Example No. | Structure | Synthesis by general method: |
|---|---|---|
| 84 | | A1 + B1 |
| 85 | 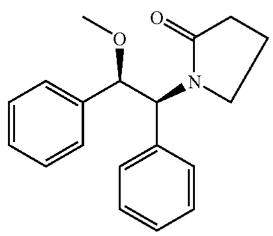 | B2 |
| 86 | | A1 + B1 |
| 87 | | A1 + B1 |
| 88 | | A2 + B2 |

-continued

| Example No. | Structure | Synthesis by general method: |
|---|---|---|
| 89 | | A1 + B1 |
| 90 | | A1 + B1 |
| 91 | | A3 + B1 |
| 92 | | A1 + B1 |

-continued

| Example No. | Structure | | Synthesis by general method: |
|---|---|---|---|
| 93 | | | A1 + B1 |
| 94 | | | A2 + B2 |
| 95 | | | A2 + B2 |
| 96 | | | A3 + B1 |

-continued

| Example No. | Structure | Synthesis by general method: |
|---|---|---|
| 97 | | A3 + B1 |
| 98 | | A1 + B1 |
| 99 | | A1 + B1 |
| 100 | | A1 + B1 |
| 101 | | A1 + B1 |

-continued
| Example No. | Structure | Synthesis by general method: |
|---|---|---|
| 102 | 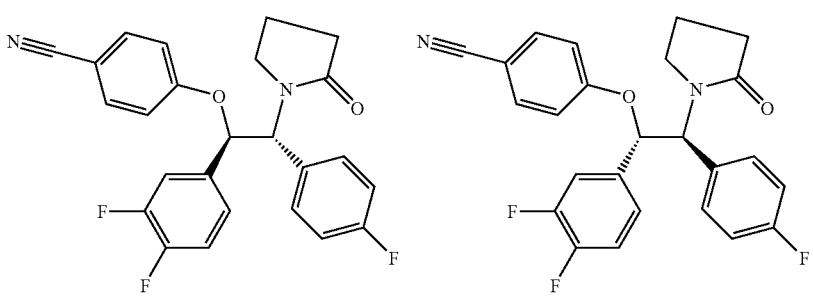 | A2 + B2 |
| 103 | 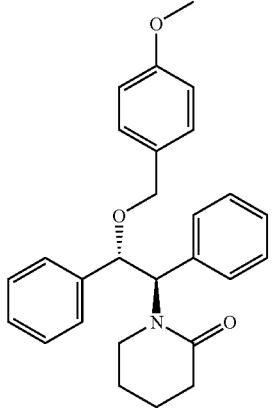 | B2 |
| 104 | 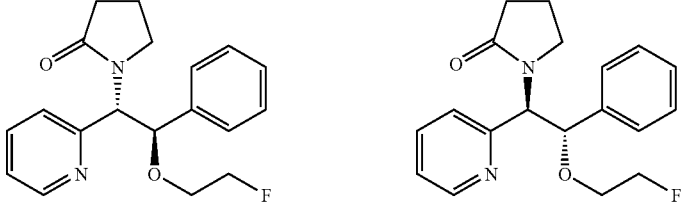 | A3 + B1 |
| 105 | 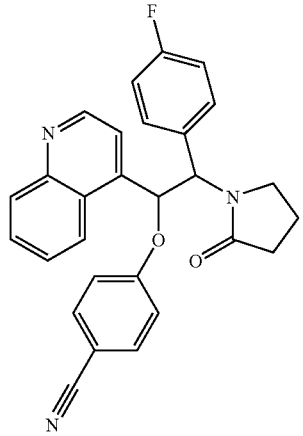 | A1 + B1 |

-continued

| Example No. | Structure | Synthesis by general method: |
|---|---|---|
| 106 | 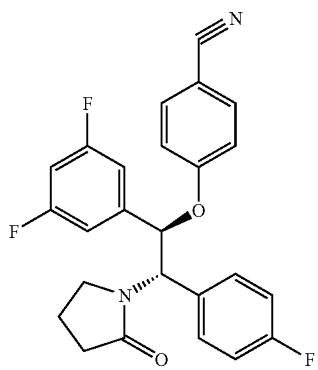 | A1 + B1 |
| 107 | 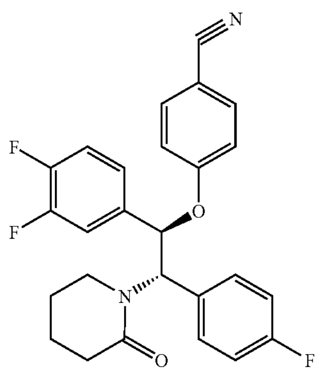 | A1 + B1 |
| 108 | 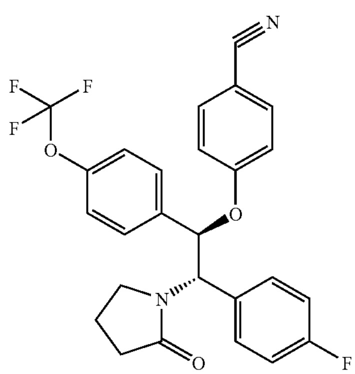 | A1 + B1 |
| 109 | 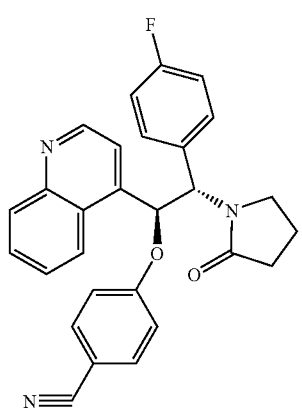 | A1 + B1 |

| Example No. | Structure | Synthesis by general method: |
|---|---|---|
| 110 | 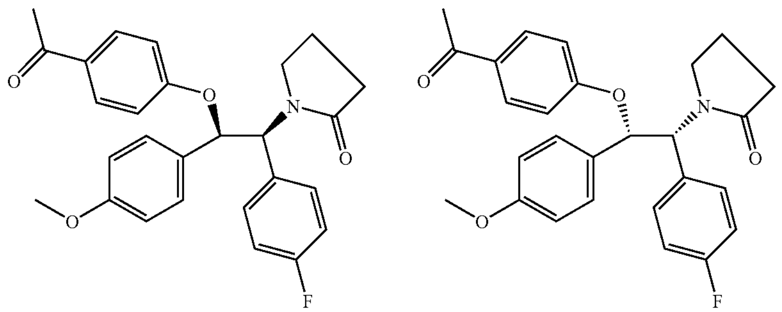 | C |
| 111 | 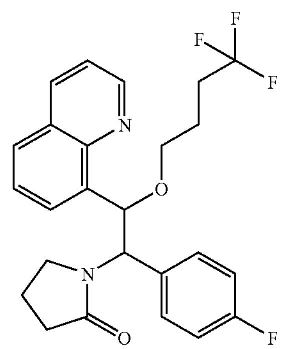 | A1 + B1 |
| 112 | 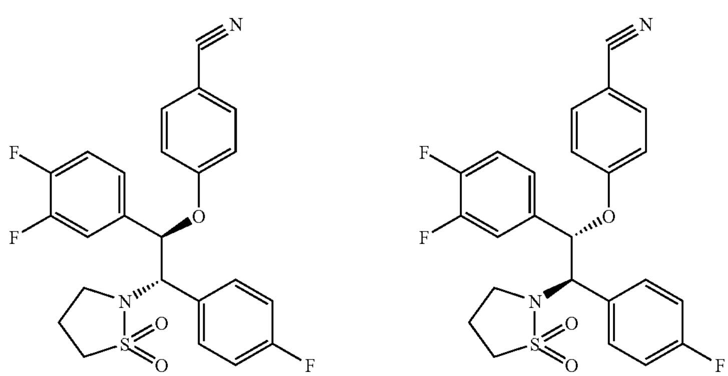 | A1 + B1 |
| 113 | 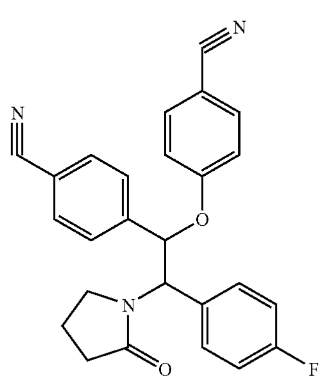 | A1 + B1 |

-continued

| Example No. | Structure | Synthesis by general method: |
|---|---|---|
| 114 | | A1 + B1 |
| 115 | | A1 + B1 |
| 116 | | A1 + B1 |
| 117 | | A1 + B1 |
| 118 | | A1 + B1 |

-continued

| Example No. | Structure | Synthesis by general method: |
|---|---|---|
| 119 | 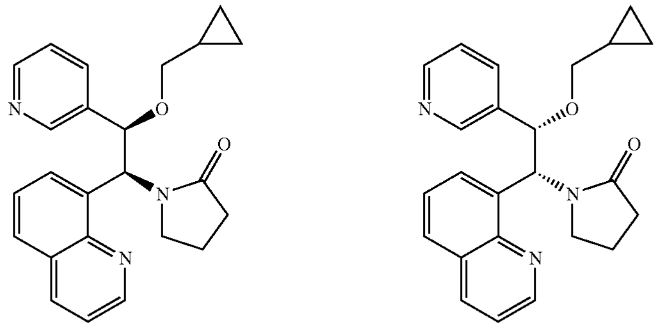 | A1 + B1 |
| 120 | 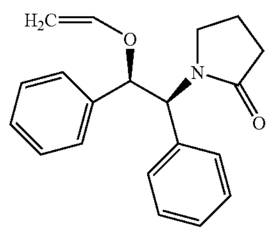 | as described above |
| 121 | 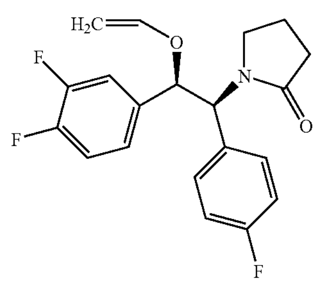 | analogous to Example 120 |

Compounds with stated absolute stereochemistry were obtained as pure enantiomers of the depicted structure. Compounds stated to be in the form of two enantiomers were obtained as racemic mixture of the two depicted enantiomers. Structures where the stereochemistry is not stated represent racemic mixtures of the possible diastereomers.

Pharmacological Investigations

Determination of the Activity on the Kv1.5 Channel

Human Kv1.5 channels were expressed in *xenopus* oocytes. For this purpose, firstly oocytes were isolated from *Xenopus laevis* and defolliculated. Kv1.5-encoding RNA synthesized in vitro was then injected into these oocytes. After Kv1.5 protein expression for 1-7 days, Kv1.5 currents were measured on the oocytes using the two-microelectrode voltage clamp technique. The Kv1.5 channels were in this case usually activated with voltage jumps lasting 500 ms to 0 mV and 40 mV. A solution of the following composition flowed through the bath: NaCl 96 mM, KCl 2 mM, $CaCl_2$ 1.8 mM, $MgCl_2$ 1 mM, HEPES 5 mM (titrated to pH 7.4 with NaOH). These experiments were carried out at room temperature. The following were employed for data acquisition and analysis: Geneclamp amplifier (Axon Instruments, Foster City, USA) and MacLab D/A converter and software (AD-Instruments, Castle Hill, Australia). The substances of the invention were tested by adding them in various concentrations to the bath solution. The effects of the substances were calculated as percent inhibition of the Kv1.5 control current which was obtained when no substance was added to the solution. The data were then extrapolated using the Hill equation in order to determine the inhibitory concentrations $IC_{50}$ for the respective substances.

Determination of the Activity on the TASK-1 Channel

Human TASK-1 channels were expressed in *xenopus* oocytes. For this purpose, firstly oocytes were isolated from *Xenopus laevis* and defolliculated. TASK-1-encoding RNA synthesized in vitro was then injected into these oocytes. After TASK-1 protein expression for 2 days, TASK-1 currents were measured on the oocytes using the two-microelectrode voltage clamp technique. The TASK-1 channels were in this case usually activated with voltage jumps lasting 250 ms to 40 mV. A solution of the following composition flowed through the bath: NaCl 96 mM, KCl 2 mM, $CaCl_2$ 1.8 mM, $MgCl_2$ 1 mM, HEPES 5 mM (titrated to pH 7.4 with NaOH). These experiments were carried out at room temperature. The following were employed for data acquisition and analysis: Geneclamp amplifier (Axon Instruments, Foster City, USA) and MacLab D/A converter and software (ADInstruments, Castle Hill, Australia). The substances of the invention were tested by adding them in various concentrations to the bath solution. The effects of the substances were calculated as percent inhibition of the TASK-1 control current which was obtained when no substance was added to the solution. The data were then extrapolated using the Hill equation in order to determine the half-maximum inhibitory concentrations ($IC_{50}$) for the respective substances.

Determination of the Activity on the KACh Channel

The effect of the substances on the acetylcholine-activated potassium channel was investigated using the micropunction technique on isolated guinea pig atria. Following sacrifice by cervical dislocation and severance of the spinal column, the heart was removed, and the left atrium was detached with fine scissors and fastened in a measuring chamber. A modified Krebs-Henseleit solution (in mmol/l: 136 NaCl, 1.0 KCl, 1.2 $KH_2PO_4$, 1.1 $MgSO_4$, 1.0 $CaCl_2$, 5 glucose, 10 HEPES, pH=7.4) flowed continuously over the tissue. The temperature in the measuring chamber was 37° C. The atrium was stimulated with a square-wave pulse of 1 to 4 volts lasting 1 to 3 milliseconds with a frequency of 1 Hz. The action potential was recorded using a glass microelectrode which was filled with 3 mol/l of KCl. The electrical signal was picked up by an amplifier (model 309 microelectrode amplifier, Hugo Sachs, March-Hugstetten, Germany) and stored and analyzed in a computer. Experimental outline: after an equilibration time of 30 min, 1 µmol/l carbachol was added in order to activate the $K_{ACh}$ ion channels by stimulating muscarinic receptors. This led to a marked shortening of the action potential duration at 90% repolarization ($APD_{90}$) of about 150 ms (without carbachol) to 50 ms after addition of carbachol (Gertjegerdes W., Ravens U., Zeigler A. (1979) Time course of carbachol-induced responses in guinea pig atria under the influence of oubain, calcium, and rate of stimulation. J. Cardiovasc. Pharmacol. 1: 235-243). Carbachol was present in the bath solution in all further measurements. After 30 min, 3 µmol/l of the substance to be measured were added and, after a further 30 min, the action potential was recorded. Blocking of $K_{ACh}$ channels leads to a prolongation of the $APD_{90}$. After a further 30 min, the substance concentration was raised to 10 µmol/l, and the measurement was carried out after an exposure time of 30 min. The percentage prolongation of the shortening of the $APD_{90}$ brought about by carbachol was calculated as the effect of the substance, the shortening by carbachol being set equal to 100%. A curve fitting was carried out with the calculated measurements using the logistic function:

$F(x)=y_o+ax^n/(c^n+x^n)$, where $c$ is the $IC_{50}$ and $n$ is the Hill coefficient.

The following $IC_{50}$ values were determined for the following compounds of formula I:

| Example No. | Kv1.5 IC-50 [µM] | mTask-1 IC-50 [µM] | KACh IC-50 [µM] |
|---|---|---|---|
| 1 | 1.4 | | 5.4 |
| 2 | 6 | | |
| 3 | 0.5 | | |
| 4 | 3.9 | 2.3 | |
| 5 | 1.3 | | |
| 6 | 0.92 | | |
| 7 | 0.6 | | |
| 8 | 1.2 | | 5.8 |
| 9 | 4.2 | 0.4 | 7.8 |
| 10 | 4.4 | | |
| 11 | 0.2 | | |
| 12 | 0.5 | | |
| 13 | 0.21 | | ~10 |
| 14 | 0.33 | | |
| 15 | 0.16 | | |
| 16 | 0.8 | | |
| 17 | 0.3 | | |
| 18 | 0.4 | | 4.2 |
| 19 | 0.3 | | |
| 20 | 0.3 | | |
| 21 | 0.8 | | |
| 22 | 0.5 | | |
| 23 | 0.65 | | |
| 24 | 0.65 | | |
| 25 | 0.45 | | |
| 26 | 1.0 | | |
| 27 | 0.6 | | ~10 |
| 28 | 0.9 | | ~10 |
| 29 | 0.9 | | |
| 30 | 1.1 | | |
| 31 | 1.4 | | |
| 32 | 0.6 | | |
| 33 | 0.9 | | |
| 34 | 1.0 | | |
| 35 | 0.5 | | |
| 36 | 0.6 | | |
| 37 | 0.7 | | |
| 38 | 0.7 | | |
| 39 | 1.1 | | 7.4 |
| 40 | 0.8 | | |
| 41 | 1.0 | | |
| 42 | 0.6 | | 4.4 |
| 43 | 1.4 | | |
| 44 | 0.5 | | |
| 45 | 1.0 | | |
| 46 | 1.5 | 5.4 | |
| 47 | 1.0 | | |
| 48 | 2.1 | | |
| 49 | 0.5 | | |
| 50 | 0.9 | | |
| 51 | 0.9 | | |
| 52 | 2.0 | | |
| 53 | 1.8 | | |
| 54 | 1.7 | | |
| 55 | 1.1 | | |
| 56 | 0.8 | | |
| 57 | 1.0 | | |
| 58 | 1.0 | | 7.7 |
| 59 | 1.9 | | 6.7 |
| 60 | 1.3 | | |
| 61 | 1.8 | | |
| 62 | 2.4 | | |
| 63 | 1.7 | | 5.6 |
| 64 | 1.83 | | |
| 65 | 1.5 | | |
| 66 | 2.3 | | |
| 67 | 1.2 | | |
| 68 | 0.5 | | |
| 69 | 1.6 | | |
| 70 | 2.3 | | |
| 71 | 1.6 | | |
| 72 | 2.1 | | |
| 73 | 1.0 | | |
| 74 | 1.4 | | |
| 75 | 1.4 | | 10.0 |
| 76 | 2.7 | | |
| 77 | 2.7 | | |
| 78 | 3.3 | | |
| 79 | 3.4 | | |
| 80 | 1.4 | | |
| 81 | 3.2 | | 5.3 |
| 82 | 3.7 | | |
| 83 | 1.8 | | |
| 84 | 2.4 | | ~10 |
| 85 | 3.6 | | |
| 86 | 2.9 | | |
| 87 | 4.2 | | |
| 88 | 4.0 | | |
| 89 | 3.5 | | |
| 90 | 4.1 | | |
| 91 | 4.0 | | |
| 92 | 3.8 | | |
| 93 | 4.1 | | |

-continued

| Example No. | Kv1.5 IC-50 [μM] | mTask-1 IC-50 [μM] | KACh IC-50 [μM] |
|---|---|---|---|
| 94 | 5.3 | | |
| 95 | 5.2 | | |
| 96 | 5.1 | | |
| 97 | 5.4 | | |
| 98 | 5.5 | | |
| 99 | 6.3 | | |
| 100 | 5.4 | | |
| 101 | 5.6 | | |
| 102 | 5.4 | | |
| 103 | 6.6 | | |
| 104 | 6.7 | | |
| 105 | 4.6 | | |
| 106 | 8.3 | | |
| 107 | 9.6 | | |
| 108 | 9.0 | | |
| 109 | 9.6 | | |
| 110 | 9.7 | | |
| 111 | 8.8 | | |
| 112 | ~10 | | |
| 113 | ~10 | | |
| 114 | ~10 | | |
| 115 | ~10 | | |
| 116 | ~10 | | |
| 117 | 0.3 | | |
| 118 | 0.8 | | |
| 119 | 0.8 | | |
| 120 | 0.8 | | |
| 121 | 0.9 | | |

What is claimed is:

1. A compound of formula I,

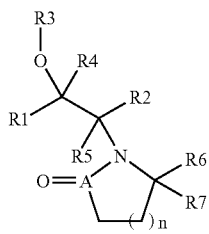

I in which:
A is C, S or S=O;
n is 0, 1, 2 or 3;
R1 is phenyl, pyridyl, thienyl, naphthyl, quinolinyl, pyrimidinyl or pyrazinyl,
where each of these aryl radicals is unsubstituted or substituted by 1, 2 or 3 substituents selected from the group consisting of F, Cl, Br, I, CN, alkoxy having 1, 2, 3 or 4 C atoms, $OCF_3$, methylsulfonyl, $CF_3$, alkyl having 1, 2, 3 or 4 C atoms, dimethylamino, sulfamoyl, acetyl, and methylsulfonylamino;
or
R1 is cycloalkyl having 3, 4, 5, 6 or 7 C atoms;
R2 is phenyl, pyridyl, thienyl, naphthyl, quinolinyl, pyrimidinyl or pyrazinyl,
where each of these aryl radicals is unsubstituted or substituted by 1, 2 or 3 substituents selected from the group consisting of F, Cl, Br, I, CN, COOMe, $CONH_2$, alkoxy having 1, 2, 3 or 4 C atoms, $OCF_3$, OH, methylsulfonyl, $CF_3$, alkyl having 1, 2, 3 or 4 C atoms, dimethylamino, sulfamoyl, acetyl, and methylsulfonylamino;
R3 is $C_pH_{2p}$—R8;
p is 0, 1, 2, 3, 4 or 5;
R8 is $CH_3$, $CH_2F$, $CHF_2$, $CF_3$, cycloalkyl having 3, 4, 5, 6 or 7 C atoms, C≡CH, C≡C—$CH_3$, alkoxy having 1, 2, 3 or 4 C atoms, phenyl or pyridyl,
where phenyl and pyridyl are unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 C atoms, alkoxy having 1, 2, 3 or 4 C atoms, dimethylamino, sulfamoyl, methylsulfonyl and methylsulfonylamino;
R4 is hydrogen or alkyl having 1, 2 or 3 C atoms;
R5 is hydrogen or alkyl having 1, 2 or 3 C atoms;
R6 and R7
are independently of one another hydrogen, F or alkyl having 1, 2, or 3 C atoms;
and the pharmaceutically acceptable salts and trifluoroacetates thereof.

2. A compound of formula I as claimed in claim 1, in which:
A is C, S or S=O;
n is 0, 1, 2 or 3;
R1 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl,
where each of these aryl radicals is unsubstituted or substituted by 1, 2 or 3 substituents selected from the group consisting of F, Cl, Br, I, CN, alkoxy having 1, 2, 3 or 4 C atoms, $OCF_3$, methylsulfonyl, $CF_3$, alkyl having 1, 2, 3 or 4 C atoms, dimethylamino, sulfamoyl, acetyl, and methylsulfonylamino;
or
R1 is cyclohexyl;
R2 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl,
where each of these aryl radicals is unsubstituted or substituted by 1, 2 or 3 substituents selected from the group consisting of F, Cl, Br, I, CN, COOMe, $CONH_2$, alkoxy having 1, 2, 3 or 4 C atoms, $OCF_3$, OH, methylsulfonyl, $CF_3$, alkyl having 1, 2, 3 or 4 C atoms, dimethylamino, sulfamoyl, acetyl, and methylsulfonylamino;
R3 is $C_pH_{2p}$—R8;
p is 0, 1, 2, 3, 4 or 5;
R8 is $CH_3$, $CH_2F$, $CHF_2$, $CF_3$, cycloalkyl having 3, 4, 5, 6 or 7 C atoms, C≡CH, C≡C—$CH_3$, alkoxy having 1, 2, 3 or 4 C atoms, phenyl or 2-pyridyl,
where phenyl and 2-pyridyl are unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 C atoms, alkoxy having 1, 2, 3 or 4 C atoms, dimethylamino, sulfamoyl, methylsulfonyl and methylsulfonylamino;
R4 is hydrogen or alkyl having 1, 2 or 3 C atoms;
R5 is hydrogen or alkyl having 1, 2 or 3 C atoms;
R6 and R7
are independently of one another hydrogen, F or alkyl having 1, 2, or 3 C atoms;

and the pharmaceutically acceptable salts and trifluoroacetates thereof.

3. A compound of formula I as claimed in claim 1, in which:

A is C or S=O;

n is 0, 1, 2 or 3;

R1 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl or 8-quinolinyl, where each of these aryl radicals is unsubstituted or substituted by 1 or 2 substituents selected from the group consisting of F, Cl, Br, I, CN, alkoxy having 1, 2, 3 or 4 C atoms, $OCF_3$, methylsulfonyl, $CF_3$ and alkyl having 1, 2, 3 or 4 C atoms;

or

R1 is cyclohexyl;

R2 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl or 8-quinolinyl, where each of these aryl radicals is unsubstituted or substituted by 1 or 2 substituents selected from the group consisting of Cl, Br, I, CN, $CF_3$, alkyl having 1, 2, 3 or 4 C atoms;

R3 is $C_pH_{2p}$—R8;

p is 0, 1, 2, 3 or 4;

R8 is $CH_3$, $CH_2F$, $CHF_2$, $CF_3$, cycloalkyl having 3, 4, 5 or 6 C atoms, C≡CH, C≡C—$CH_3$, alkoxy having 1, 2, 3 or 4 C atoms, phenyl or 2-pyridyl, where phenyl and 2-pyridyl are unsubstituted or substituted by 1 or 2 substituents selected from the group consisting of F, Cl, Br, I, $CF_3$, $OCF_3$, CN, COOMe, $CONH_2$, COMe, OH, alkyl having 1, 2, 3 or 4 C atoms and alkoxy having 1, 2, 3 or 4 C atoms;

R4 is hydrogen or alkyl having 1, 2 or 3 C atoms;

R5 is hydrogen or alkyl having 1, 2 or 3 C atoms;

R6 and R7 are independently of one another hydrogen, F or alkyl having 1, 2, or 3 C atoms;

and the pharmaceutically acceptable salts and trifluoroacetates thereof.

4. A pharmaceutical composition comprising a pharmaceutically effective amount of at least one compound of formula I as claimed in claim 1 or a pharmaceutically acceptable salt thereof as active ingredient, together with one or more pharmaceutically acceptable carriers or additives.

5. A pharmaceutical composition comprising an effective amount of at least one compound of formula I as claimed in claim 1 or a pharmaceutically acceptable salt thereof as active ingredient, together with one or more pharmaceutically acceptable carriers or additives, and in combination with one or more other pharmacologically active ingredients or pharmaceuticals.

6. A pharmaceutical composition comprising a pharmaceutically effective amount of at least one compound of formula I as claimed in claim 1, or a pharmaceutically acceptable salt thereof, and a beta blocker as active ingredients, together with one or more pharmaceutically acceptable carriers or additives.

7. A pharmaceutical composition comprising a pharmaceutically effective amount of at least one compound of formula I as claimed in claim 1, or a pharmaceutically acceptable salt thereof, and an IKs channel blocker as active ingredients, together with one or more pharmaceutically acceptable carriers or additives.

* * * * *